(12) United States Patent
Battista, Jr.

(10) Patent No.: US 9,380,982 B2
(45) Date of Patent: Jul. 5, 2016

(54) ADAPTIVE ALARM SYSTEM AND METHOD

(75) Inventor: John A. Battista, Jr., Lafayette, CO (US)

(73) Assignee: COVIDIEN LP, Mansfield, MA (US)

( * ) Notice: Subject to any disclaimer, the term of this patent is extended or adjusted under 35 U.S.C. 154(b) by 985 days.

(21) Appl. No.: 12/845,196

(22) Filed: Jul. 28, 2010

(65) Prior Publication Data

US 2012/0029301 A1 Feb. 2, 2012

(51) Int. Cl.
*A61B 5/00* (2006.01)
*G06F 19/00* (2011.01)
*A61B 5/1455* (2006.01)

(52) U.S. Cl.
CPC .............. *A61B 5/746* (2013.01); *A61B 5/14551* (2013.01); *G06F 19/3406* (2013.01); *G06F 19/345* (2013.01)

(58) Field of Classification Search
CPC ........... H03G 3/32; H03G 5/00; H03G 7/002; H03G 9/00; H04R 1/00; H04R 3/00; H04R 2201/00; H04R 2203/00; G10K 7/00; G10K 11/00; G10K 15/00; G06F 19/3406; G06F 3/16

See application file for complete search history.

(56) References Cited

U.S. PATENT DOCUMENTS

| | | | |
|---|---|---|---|
| 3,579,233 A * | 5/1971 | Raschke | 340/384.72 |
| 3,638,640 A | 2/1972 | Shaw | |
| 4,047,377 A * | 9/1977 | Banks, Jr. | 368/12 |
| 4,936,679 A | 6/1990 | Mersch | |
| 4,971,062 A | 11/1990 | Hasebe et al. | |
| 4,974,591 A | 12/1990 | Awazu et al. | |
| 5,028,787 A | 7/1991 | Rosenthal et al. | |
| 5,065,749 A | 11/1991 | Hasebe et al. | |
| 5,084,327 A | 1/1992 | Stengel | |
| 5,275,159 A | 1/1994 | Griebel | |
| 5,483,646 A | 1/1996 | Uchikoga | |
| 5,576,685 A * | 11/1996 | Saito | 340/384.1 |
| 5,730,124 A | 3/1998 | Yamauchi | |
| 5,779,631 A | 7/1998 | Chance | |
| 5,830,139 A | 11/1998 | Abreu | |
| 5,831,598 A | 11/1998 | Kauffert et al. | |
| 5,871,442 A | 2/1999 | Madarasz et al. | |
| 5,873,821 A | 2/1999 | Chance et al. | |

(Continued)

FOREIGN PATENT DOCUMENTS

| | | | |
|---|---|---|---|
| JP | 1 103308 A | | 4/1989 |
| JP | 02036489 A | * | 2/1990 |

(Continued)

OTHER PUBLICATIONS

International Search Report and Written Opinion for PCT Application No. PCT/US2011/045540 dated Nov. 11, 2011; 11 pgs.

(Continued)

*Primary Examiner* — Gary Jackson
*Assistant Examiner* — Shirley Jian
(74) *Attorney, Agent, or Firm* — Fletcher Yoder PC

(57) ABSTRACT

An adaptive-alarm system and its uses in the context of medical devices, such as patient monitors, are described. In one embodiment, the monitor has a processor configured to receive and analyze an input relating to ambient sounds. The monitor may generate an alarm signal in response to physiological data that meets a defined requirement, such as a physiological alarm condition. The alarm signal that is generated by the monitor is substantially free of masking by the ambient sounds.

18 Claims, 9 Drawing Sheets

(56) References Cited

U.S. PATENT DOCUMENTS

| | | | |
|---|---|---|---|
| 6,081,742 | A | 6/2000 | Amano et al. |
| 6,120,460 | A | 9/2000 | Abreu |
| 6,134,460 | A | 10/2000 | Chance |
| 6,285,895 | B1 | 9/2001 | Ristolainen et al. |
| 6,312,393 | B1 | 11/2001 | Abreu |
| 6,353,750 | B1 | 3/2002 | Kimura et al. |
| 6,415,236 | B2 | 7/2002 | Kobayashi et al. |
| 6,419,671 | B1 | 7/2002 | Lemberg |
| 6,461,305 | B1 | 10/2002 | Schnall |
| 6,487,439 | B1 | 11/2002 | Skladnev et al. |
| 6,544,193 | B2 | 4/2003 | Abreu |
| 6,549,795 | B1 | 4/2003 | Chance |
| 6,591,122 | B2 | 7/2003 | Schmitt |
| 6,606,509 | B2 | 8/2003 | Schmitt |
| 6,618,042 | B1 | 9/2003 | Powell |
| 6,622,095 | B2 | 9/2003 | Kobayashi et al. |
| 6,662,030 | B2 | 12/2003 | Khalil et al. |
| 6,675,029 | B2 | 1/2004 | Monfre et al. |
| 6,684,090 | B2 | 1/2004 | Ali et al. |
| 6,687,519 | B2 | 2/2004 | Steuer et al. |
| 6,690,958 | B1 | 2/2004 | Walker et al. |
| 6,714,245 | B1 | 3/2004 | Ono |
| 6,731,274 | B2 | 5/2004 | Powell |
| 6,785,568 | B2 | 8/2004 | Chance |
| 6,793,654 | B2 | 9/2004 | Lemberg |
| 6,850,053 | B2 | 2/2005 | Daalmans et al. |
| 6,898,451 | B2 | 5/2005 | Wuori |
| 6,947,780 | B2 | 9/2005 | Scharf |
| 6,949,081 | B1 | 9/2005 | Chance |
| 6,996,427 | B2 | 2/2006 | Ali et al. |
| 7,024,233 | B2 | 4/2006 | Ali et al. |
| 7,035,697 | B1 | 4/2006 | Brown |
| 7,041,063 | B2 | 5/2006 | Abreu |
| 7,043,289 | B2 | 5/2006 | Fine et al. |
| 7,065,392 | B2 | 6/2006 | Kato |
| 7,095,491 | B2 | 8/2006 | Forstner et al. |
| 7,123,950 | B2 | 10/2006 | Mannheimer |
| 7,173,525 | B2 | 2/2007 | Albert |
| 7,236,811 | B2 | 6/2007 | Schmitt |
| 7,239,902 | B2 | 7/2007 | Scmitt et al. |
| 7,272,426 | B2 | 9/2007 | Schmid |
| 7,398,115 | B2 | 7/2008 | Lynn |
| 7,469,158 | B2 | 12/2008 | Cutler et al. |
| 7,551,950 | B2 | 6/2009 | Cheng |
| 7,621,877 | B2 | 11/2009 | Schnall |
| 8,144,909 | B2 * | 3/2012 | Hillbratt et al. ............... 381/326 |
| 2002/0042558 | A1 | 4/2002 | Mendelson |
| 2002/0156354 | A1 | 10/2002 | Larson |
| 2002/0190863 | A1 | 12/2002 | Lynn |
| 2002/0198443 | A1 | 12/2002 | Ting |
| 2003/0023140 | A1 | 1/2003 | Chance |
| 2004/0133087 | A1 | 7/2004 | Ali et al. |
| 2004/0171920 | A1 | 9/2004 | Mannheimer et al. |
| 2005/0033128 | A1 | 2/2005 | Ali et al. |
| 2005/0113651 | A1 | 5/2005 | Wood et al. |
| 2005/0113656 | A1 | 5/2005 | Chance |
| 2005/0192488 | A1 | 9/2005 | Bryenton et al. |
| 2005/0228248 | A1 | 10/2005 | Dietiker |
| 2006/0017558 | A1 | 1/2006 | Albert et al. |
| 2006/0020181 | A1 | 1/2006 | Schmitt |
| 2006/0195025 | A1 | 8/2006 | Ali et al. |
| 2006/0247501 | A1 | 11/2006 | Ali |
| 2007/0032714 | A1 | 2/2007 | Mannheimer et al. |
| 2008/0091090 | A1 | 4/2008 | Guillory et al. |
| 2008/0091092 | A1 | 4/2008 | Al-Ali |
| 2008/0161063 | A1 | 7/2008 | Schuster et al. |
| 2008/0183057 | A1 | 7/2008 | Taube |
| 2008/0183058 | A1 | 7/2008 | Mannheimer |
| 2009/0146799 | A1 | 6/2009 | Goldstein et al. |
| 2010/0157018 | A1 * | 6/2010 | Lampotang et al. ............ 348/36 |

FOREIGN PATENT DOCUMENTS

| | | |
|---|---|---|
| JP | 2003248058 A | 9/2003 |
| WO | WO9309711 | 5/1993 |

OTHER PUBLICATIONS

A. Johansson; "Neural network for photoplethysmographic respiratory rate monitoring," *Medical & Biological Engineering & Computing*, vol. 41, pp. 242-248 (2003).

Active Matrix ePaper Displays; Innovating Display Solutions; SiPix.

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Barreto, Armando B., et al.; "Adaptive LMS Delay Measurement in dual Blood Volume Pulse Signals for Non-Invasive Monitoring," *IEEE*, pp. 117-120 (1997).

Belal, Suliman Yousef, et al.; "A fuzzy system for detecting distorted plethysmogram pulses in neonates and paediatric patients," *Physiol. Meas.*, vol. 22, pp. 397-412 (2001).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Cysewska-Sobusaik, Anna; "Metrological Problems With noninvasive Transillumination of Living Tissues," *Proceedings of SPIE*, vol. 4515, pp. 15-24 (2001).

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.

Electronic Paper Displays; E Ink Corporation; 2005.

First-Generation Electronic Paper Display from Phlips, Sony and E Ink to be Used in New Electronic Reading Devices; E Ink Corporation; 2005.

Goldman, Julian M.; "Masimo Signal Extraction Pulse Oximetry," *Journal of Clinical Monitoring and Computing*, vol. 16, pp. 475-483 (2000).

Hamilton, Patrick S., et al.; "Effect of Adaptive Motion-Artifact Reduction on QRS Detection," *Biomedical Instrumentation & Technology*, pp. 197-202 (undated).

J. Huang, et al.; "Low Power Motion Tolerant Pulse Oximetry," *Abstracts*, A7, p. S103. (undated).

Kaestle, S.; "Determining Artefact Sensitivity of New Pulse Oximeters in Laboratory Using Signals Obtained from Patient," *Biomedizinische Technik*, vol. 45 (2000).

Kim, J.M., et al.; "Signal Processing Using Fourier & Wavelet Transform," pp. II-310-II-311 (updated).

Leahy, Martin J., et al.; "Sensor Validation in Biomedical Applications," *IFAC Modelling and Control in Biomedical Systems*, Warwick, UK; pp. 221-226 (1997).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Lutter, Norbert O., et al.; "False Alarm Rates of Three Third-Generation Pulse Oximeters in PACU, ICU and IABP Patients," *Anesth Analg*, vol. 94, pp. S69-S75 (2002).

(56) References Cited

OTHER PUBLICATIONS

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Odagiri, Y.; "Pulse Wave Measuring Device," *Micromechatronics*, vol. 42, No. 3, pp. 6-11 (undated) (Article in Japanese—contains English summary of article).

Plastic Logic;http://www.plasticlogic.com/product.html ; 2000.

R. Neumann, et al.; "Fourier Artifact suppression Technology Provides Reliable SpO$_2$," *Abstracts*, A11, p. S105. (undated).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Segmented ePaper Displays; Innovating Display Solutions; SiPix.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

\* cited by examiner

US 9,380,982 B2

ADAPTIVE ALARM SYSTEM AND METHOD

BACKGROUND

The present disclosure relates generally to alarm systems for patient physiological data monitoring instruments. In particular, the present disclosure relates to an adaptive alarm system including features for monitoring ambient sounds and generating an alarm suitable for use in a given environment.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, caregivers often monitor certain physiological characteristics of their patients. Accordingly, a wide variety of devices have been developed for monitoring many such characteristics of a patient. Such monitoring devices provide caregivers, such as doctors, nurses, paramedics, and other healthcare personnel with information they may need in order to provide the best possible healthcare for their patients. As a result, such monitoring devices have become an indispensable part of modern medicine.

Medical devices include patient monitors that facilitate measurement and observation of patient physiological data. These patient monitors may be used in a number of settings, such as patient rooms, emergency rooms, ambulances, emergency helicopters, and so on. For example, pulse oximeters are a type of patient monitor that may be employed in such settings. A typical patient monitor cooperates with a sensor to detect and display a patient's vital signs (e.g., temperature, pulse rate, respiratory rate) and/or other physiological measurements (e.g., water content of tissue, blood oxygen level) for observation by a user (e.g., clinician). In the case of a pulse oximeter, it is generally utilized with related sensors to detect and monitor a patient's functional oxygen saturation of arterial hemoglobin (i.e., $SpO_2$) and pulse rate. Other types of patient monitors, such as blood pressure monitors, may be utilized to detect and monitor other physiological parameters. Further, the patient monitors may be incorporated into other types of medical devices, such as mechanical ventilators and anesthesia machines, among others.

A patient monitor may be designed to alert a caregiver when certain physiological conditions are recognized. For example, a pulse oximeter may produce a visual and/or audible alarm when a patient's oxygen saturation exceeds or dips below a predetermined threshold. In certain situations, an audible alarm may be used when a caregiver is not in a patient's room or is away from the patient. Further, a patient monitor may be designed to provide different audible alarms representative of various indications. For example, a patient monitor may sound one alarm in response to a set of data that is representative of a disconnection (i.e., a sensor has been removed from the patient), while sounding a different alarm when measured physiological data indicates a medical condition. Additionally, if the monitor is battery-powered, the patient monitor may sound a notification alarm when battery charge is low. Indeed, these original alarms may be based on multiple variables and may interact with alarms from other monitors or sounds from a surrounding environment. In these situations, a caregiver may have trouble hearing or recognizing the sounded original alarm.

BRIEF DESCRIPTION OF THE DRAWINGS

Advantages of the disclosed techniques may become apparent upon reading the following detailed description and upon reference to the drawings in which.

DETAILED DESCRIPTION

Figure 1:
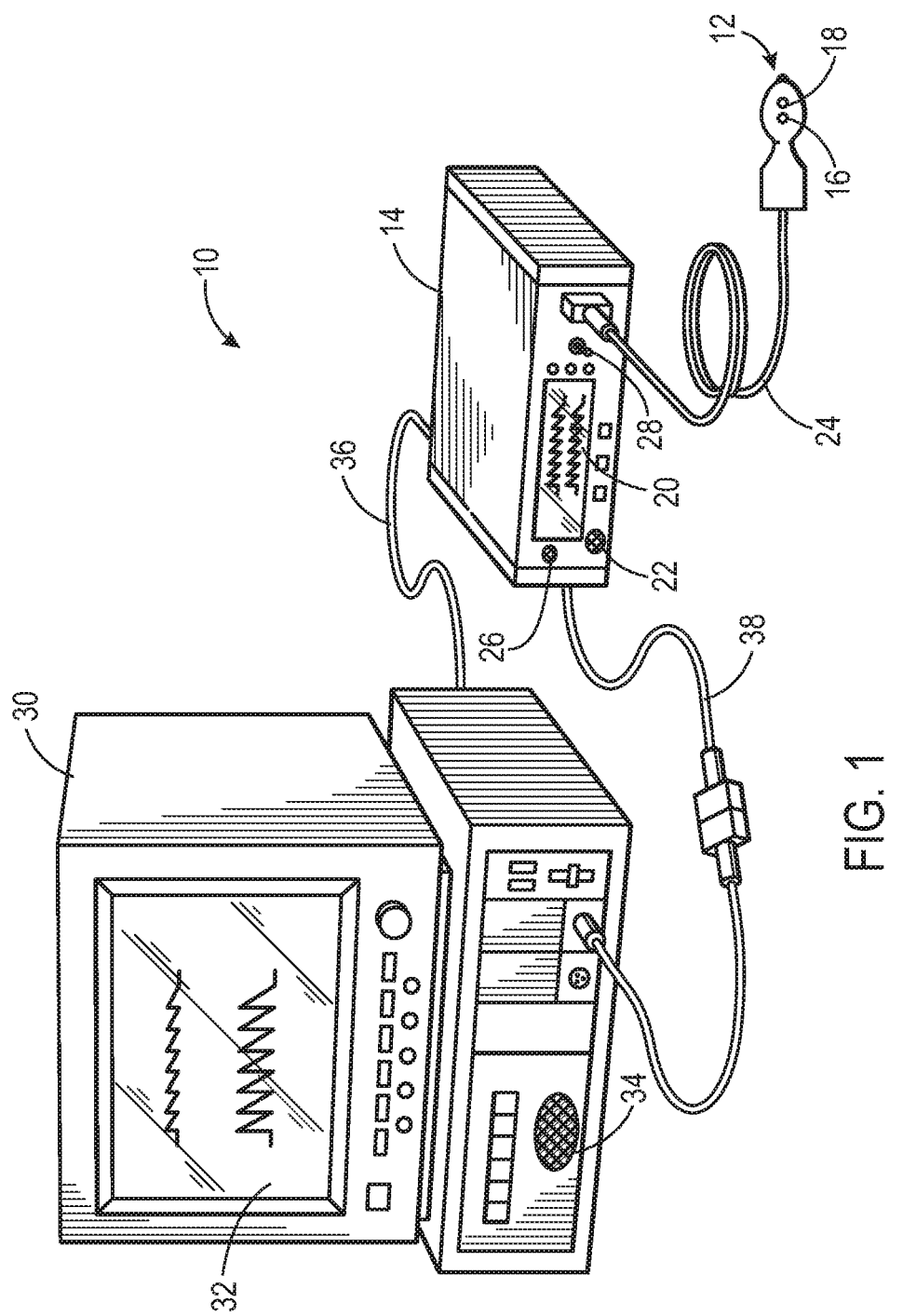
FIG. 1 is a perspective view of an embodiment of a pulse oximetry system having a pulse oximetry monitor with an adaptive alarm system, in accordance with an aspect of the present technique.

One or more embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure relates to mitigating of the effect of ambient sounds on the alarms of medical devices. For example, a caregiver may encounter ambient sounds that interfere with or mask an original alarm of a given medical device. To counteract such interference or masking, medical devices may be adapted to include sound analysis features for generating one or more modified alarms that are substantially unaffected by the ambient sounds. Such medical devices may be referred to as having adaptive alarm capabilities, and can include medical devices such as vital sign, pulse oximetry, respiratory, blood pressure, and other patient monitors and therapeutic devices such as ventilators, defibrillators, resuscitation systems, counterpulsation devices, neuromodulation devices, and so on.

Medical devices with adaptive-alarm capabilities may include one or more processing components for analyzing ambient sounds. In response to the analysis, the processing components may allow the medical device to generate an alarm that is substantially free of masking by the ambient sounds. As an example, the processing components may modify one or more frequencies and/or adjust the volume of an original alarm. Accordingly, based on the analysis of the ambient sounds, the alarm may be volume-adjusted in lieu of or in combination with new alarm generation, selection of a pre-generated alarm from a table, or modification of the original alarm.

The process by which a modified alarm is generated or selected may depend on a variety of factors, including the extent to which ambient sounds are interfering with or masking the original alarm, the nature and complexity of the original alarm, various user inputs, and/or adherence to collateral safety standards (e.g., I.E.C. 60601-1-8). In certain embodiments, a user may adjust the alarm settings of the medical device by providing an input as to the nature of the ambient sounds. For example, the user may input, as a user-adjusted alarm setting, that a specific set of sounds are present such as those produced by an ambulance siren or spinning helicopter blades. The user-adjusted alarm setting may result in a pre-configured response by the processing components of the medical device. In this way, a paramedic or other emergency responder working in the field may switch the medical device into modes such as an "ambulance mode," which may provide an input to the medical device. The input may direct the processing components of the medical device to select a pre-generated alarm from a set of alarms, with the selected alarm (or set of alarms) being substantially free of masking by the ambulance siren or other common sounds associated with an ambulance. In other situations, such as when switched to a "helicopter mode," the input may result in a selected, pre-generated alarm that is substantially free of masking by helicopter sounds, and so on.

Another user input may set the medical device into a "detection mode" that allows the medical device to determine an appropriate response to the ambient sounds. In detection mode, a microphone, which may be built into or connected to the medical device, may capture ambient sounds from the surrounding environment. The microphone may deliver a signal representative of the ambient sounds to the processing components of the medical device for analysis. The analysis may include, for example, performing a Fast Fourier Transform (FFT) on the signal to generate a frequency spectrum. Further, only frequencies within the audible range of humans may be analyzed, such that certain frequencies are filtered out. For example, in embodiments where the signal is digitized, the range may include a frequency range that is at least approximately twice the upper limit of the selected audible range (i.e., the human audible range), such that the audible range may be accurately analyzed and/or reproduced. Alternatively or additionally, if the signal is analog, the range may include substantially only the human audible range. The audible range may include a frequency range and a volume range (such as those frequencies having a volume measurement above a predefined threshold). The filtered frequencies of the ambient sounds may be compared to those of the original alarm (and other stored alarms if applicable) to determine the extent to which the original and/or stored alarms are masked by (i.e., overlap with) the ambient sounds. Additionally or alternatively, the masking may be volume-related. That is, even when the frequencies of the ambient sounds do not substantially overlap with the original alarm frequencies, the ambient sounds may be sufficiently loud (have sufficient power) to mask the original alarm frequencies. Where the filtered frequencies of the ambient sounds mask one or more frequencies of the original and/or stored alarms, the original alarm may be modified or a new alarm may be generated accordingly.

Although the techniques introduced above and discussed in detail below may be implemented for a variety of medical devices, the present disclosure will discuss the implementation of these techniques in a pulse oximetry system. FIG. 1 is a perspective view of an embodiment of such a pulse oximetry system 10. The system 10 includes a sensor 12 and a pulse oximetry monitor 14, which may have adaptive-alarm capabilities, as discussed below. The sensor 12 may include an emitter 16 for emitting light at one or more wavelengths toward a patient's tissue and a detector 18 for detecting the light passing through, reflected or fluoresced by the tissue of the patient. The pulse oximetry monitor 14 may be configured to calculate physiological parameters received from the sensor 12 relating to light emission and detection. Further, the pulse oximetry monitor 14 includes a display 20 configured to display the physiological parameters, other information about the system, alarm indications, and/or alarm modes. The pulse oximetry monitor 14 also includes a speaker 22 to provide an audible alarm in the event that the patient's physiological parameters are not within a normal range, as defined based on patient characteristics. It should be noted, however, that in some embodiments the pulse oximetry monitor 14 may be connected to, rather than contain, a speaker for sounding the alarm. The sensor 12 is communicatively coupled to the pulse oximetry monitor 14 via a cable 24. However, in other embodiments a wireless transmission device or the like may be utilized instead of or in addition to the cable 24.

As noted above, the pulse oximetry monitor 14 may have adaptive-alarm capabilities. Therefore, in addition to the features described above, in certain embodiments the pulse oximetry monitor 14 may also include a microphone 26 that is configured to sample acoustics of the surrounding environment (ambient sounds). The microphone 26 may be a microphone on a chip, a built-in microphone, or any device capable of acting as a transducer to convert the ambient sounds into an electrical signal. In other embodiments, the pulse oximetry monitor 14 may be connected to an external microphone, rather than contain a built-in microphone. In one embodiment, the speaker 22 may act as a transducer, which may allow the speaker 22 to act as the microphone 26. According to situation-specific embodiments, the microphone 26 may sample the ambient sounds substantially continuously, or may sample the ambient sounds at intervals (periodically), for example to conserve battery power. Nevertheless, the microphone 26 may provide a signal representative of the ambient sounds to one or more processing components of the pulse oximetry monitor 14 for analysis. The processing components may analyze the frequencies and/or volumes of the ambient sounds and then compare them to the original alarm stored in the pulse oximetry monitor 14. Where the frequencies of the ambient sounds are above a pre-determined energy threshold (i.e., above a certain volume), the pulse oximetry monitor 14 may generate a modified alarm. For example, frequencies having amplitudes sufficient to mask frequencies of the original alarm may result in a modified alarm generation by the pulse oximetry monitor 14, such that the modified alarm is substantially free of masking by the ambient sounds. Where the frequencies and their energies of the ambient sounds are relatively or substantially negligible, the pulse oximetry monitor 14 may sound the original alarm.

The pulse oximetry monitor 14 may generate the modified alarm "on the fly" (i.e., in substantially real time, such as in less than approximately 5 seconds), may adjust an existing alarm (an original alarm) by adjusting tone, pitch, and/or volume, or may select a pre-generated alarm from a list or table. The pulse oximetry monitor 14 may also adjust the volume of whichever alarm is used to a level suitable for user recognition. The method in which the pulse oximetry monitor 14 generates the modified alarm may depend on a number of factors, including the setting in which the pulse oximetry monitor 14 is employed, the particular configuration of the pulse oximetry monitor 14, user input, or any combination of these and other factors.

To allow a user to provide alarm-related input, the pulse oximetry monitor 14 may include a mode switch 28. As an example, the mode switch 28 may allow the user to choose between an "ambulance mode," a "helicopter mode," a "hospital mode," a "stadium mode," and so forth. In each mode, the pulse oximetry monitor 14 may contain a pre-configured response to the nature and relative volume of ambient sounds characteristic of the selected setting. For example, the "hospital mode" may include a pre-configured response that takes into account other possible hospital alarms, communication between people, equipment noise, and so on. In another example, the "ambulance mode" may take into account an ambulance siren, vehicular noise, and the like. Indeed, some modes may generate a modified alarm that is merely a volume adjustment of the original alarm, while other modes may generate modified alarms that may be substantially new. Further, some modes may generate a modified alarm having both volume and alarm tone adjustment. In embodiments according to the present technique, the pre-configured response may result in the selection of a pre-generated alarm from a table and the adjustment of the volume of the selected alarm to a suitable level.

While the mode switch 28 may allow a user to select between pre-configured responses, other features on the pulse oximetry monitor 14 or to which the pulse oximetry monitor 14 is connected may allow a higher degree of functionality, such that a user is able to provide detailed information about ambient sounds, re-configure adaptive-alarm features, set volume thresholds, and so forth. In the illustrated embodiment, such functionality may be provided by a multi-parameter patient monitor 30. The multi-parameter patient monitor 30 may include a computer or similar processing-relating equipment, and is generally configured to calculate physiological parameters and to provide a display 32 for information from the pulse oximetry monitor 14 and from other medical monitoring devices or systems. In the present context, the multi-parameter patient monitor 30 may allow a user to address the pulse oximetry monitor 14 to re-program modes, set frequency and volume thresholds, re-program stored alarms, manually adjust alarms, and so forth. Additionally, the central display 32 may allow the user to view current mode settings, view real-time frequency spectra, and view alarm tables and sort them as desired, among others. In some configurations, the pulse oximetry monitor 14 may cause the multi-parameter patient monitor 30 to generate a modified alarm. That is, the pulse oximetry monitor 14 may provide adaptive-alarm capability to the multi-parameter patient monitor 30, which may allow the multi-parameter patient monitor 30 to generate a modified alarm in response to an alarm condition detected by another patient monitor other than the pulse oximetry monitor 14. The modified alarm so generated may be sounded by the speaker 22 on the pulse oximetry monitor 14, or a speaker 34 built into the multi-parameter patient monitor 30. Indeed, the speaker 34 may perform the functions described above with regard to the speaker 22 and/or the microphone 26 built in to the pulse oximetry monitor 14. Additionally, the multi-parameter patient monitor 30 may generate a visible or audible alarm via the display 32 or the speaker 34, respectively, if the patient's physiological characteristics are found to be outside of the expected range. The pulse oximetry monitor 14 may be communicatively coupled to the multi-parameter patient monitor 30 via a cable 36 or 38 or coupled to a sensor input port or a digital communications port, respectively. In addition, the pulse oximetry monitor 14 and/or the multi-parameter patient monitor 30 may be connected to a network to enable the sharing of information with servers or other workstations.

Figure 2:
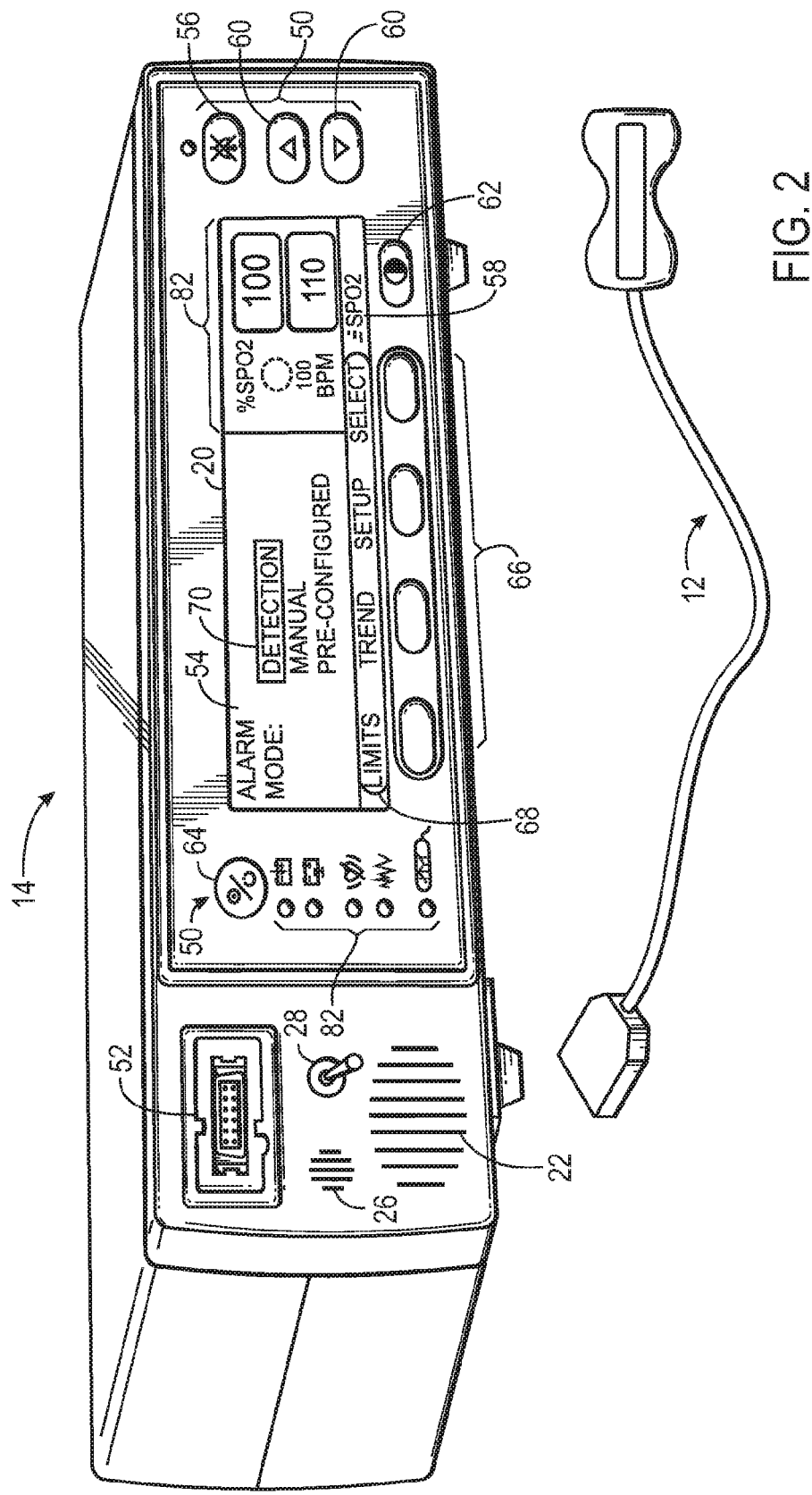
FIG. 2 is a front view of an embodiment of a pulse oximetry monitor having an adaptive alarm system, in accordance with one aspect of the present technique.

FIG. 2 is a perspective view illustrating various features of the pulse oximetry monitor 14 that may allow a user to interface with and control adaptive-alarm functions. In addition to or in lieu of the mode switch 28, a user may actuate inputs 50 to control operation of the pulse oximetry monitor 14 and to switch between, select, and configure various alarm modes. For example, a user may input volume and tone settings, or may use the inputs 50 to create new "modes." The selectable inputs 50 may include buttons that may be pressed to change information shown on the display 20, which may be a cathode ray tube or liquid crystal display. Moreover, the display 20 may include a touch screen that allows a user to provide input.

In general use, as noted above with respect to FIG. 1, the display 20 may show processed plethysmographic data (i.e. a plethysmographic waveform) and/or other data received through a sensor interface 52 from the pulse oximetry sensor 12. The display 20 may also display user interface options, such as a setup and/or configuration screen for adjusting parameters related to the adaptive-alarm features, such as alarm modes, frequencies, volumes, and tones, among others. In the illustrated embodiment, the display 20 is illustrated as showing a mode menu 54, which may list a number of modes from which the user may select, including the "detection" mode, a "manual" mode, a "pre-configured" mode, and a "volume" mode. The selection of such modes is discussed in further detail below.

The display 20 may also include an alarm status indicator such as a bell that flashes when an alarm condition is present, or if the adaptive alarm system has been activated. One of the input devices, such as an alarm silence button 56, may be actuated to silence the alarm and display an alarm silence indicator such as a slash and a timer, on the display 20. The display 20 also may show monitoring mode setting information describing a specific monitoring mode to which alarm limits are set. In another example, the display 24 may show an indicator 58 that informs a caretaker that the pulse oximetry monitor 14 is operating in a fast alarm response mode rather than a normal alarm mode. In such embodiments, the fast alarm response mode may direct the processing components within the pulse oximetry monitor 14 to select an alarm from a table, rather than generate an alarm on the fly.

As noted above, to change information provided on the display 24 and to control operating functions of the pulse oximetry monitor 14, a user may press or actuate the inputs 50. The selectable inputs 50 may include fixed function keys, such as the alarm silence button 56 described above, arrow keys 60, a contrast selection key 62, and a power key 64. For example, the arrow keys 60 may be actuated to adjust alarm limits and/or to act as part of the mode switch 28. In another example, the contrast selection key 62 may be actuated to adjust the contrast of the display 20. Further, the inputs 50 may be programmed to control multiple functions or to operate in different manners based upon various factors, such as the duration the key is pressed, the simultaneous activation of other keys, and so forth. For example, an arrow key 60 may be configured to scroll upwards or downwards more rapidly based upon how long the respective key is held down.

Figure 2A:
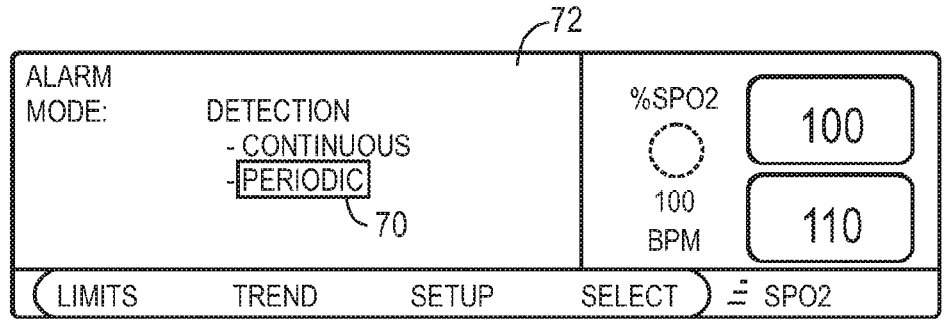
FIG. 2A is a front view of an embodiment of the pulse oximetry monitor of FIG. 2 after selecting the PRE-CONFIGURED mode, in accordance with one aspect of the present technique.
Figure 2B:
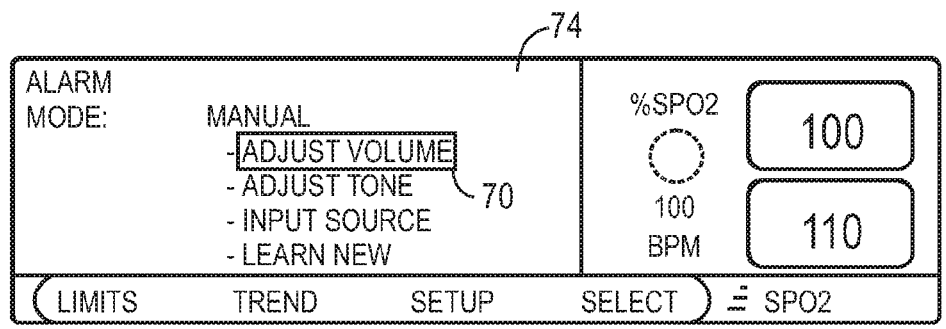
FIG. 2B is a front view of an embodiment of the pulse oximetry monitor of FIG. 2 after selecting the DETECTION mode, in accordance with one aspect of the present technique.
Figure 2C:
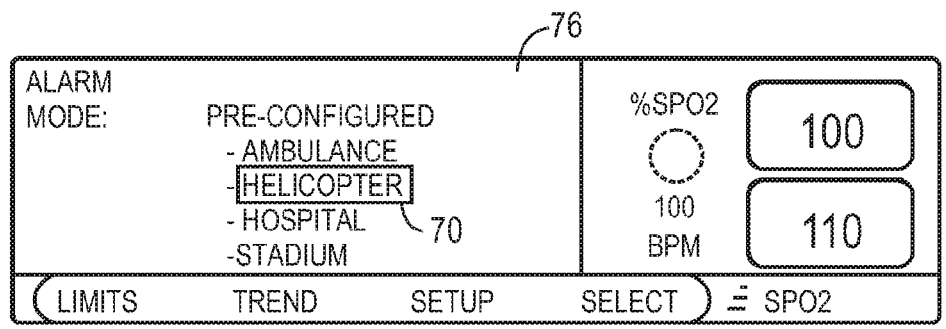
FIG. 2C is a front view of an embodiment of the pulse oximetry monitor of FIG. 2 after selecting the MANUAL mode, in accordance with one aspect of the present technique.

The inputs 50 may also include programmable function keys ("soft keys") 66, and associated soft key icons in the soft key menu 68. Each of the soft keys may be pressed to select a corresponding function indicated by the respective soft key icon. For example, the soft keys may be pressed to display alarm limits information, patient physiological trend information, setup menus, and adaptive alarm settings, among others. In one embodiment according to the present techniques, actuating the soft keys 66 may access the adaptive alarm mode menu 54, which a user may navigate using the arrow keys 60 to choose between modes, adjust volume or energy thresholds, input sources of ambient noise, and so forth. That is, the soft keys 66 together with the arrow keys 60 may act in a similar manner to the mode switch 28. In an example use, a user may access the mode menu 54 using the mode switch 28 and/or one or more soft keys 66. The user may move a cursor or highlight 70 over one of the listed modes and select a desired mode by pressing one or more of the soft keys 66 and/or a combination of the arrows 60. The selected modes, which in the illustrated embodiment include "DETECTION," "MANUAL," and "PRE-CONFIGURED," are shown in FIGS. 2A-2C, respectively, as example illustrations of the information provided on the display 20 upon accessing each listed mode.

In the illustrated embodiment, the highlight 70 is shown as highlighting the "DETECTION" mode. In embodiments where the user selects the "detection" mode, for example by actuating a "SELECT" soft key, a detection mode screen 72, an embodiment of which is illustrated in FIG. 2A, is displayed. A variety of options may be listed on the detection mode screen 72, such as a "continuous" option and a "periodic" option. As an example, the "continuous" option may direct the pulse oximetry monitor 14 to monitor (i.e., capture via microphone 26 and analyze via processing circuitry) ambient sounds substantially continuously, such that there is no lapse in ambient noise processing. Such an option may be desirable in settings that experience rapid changes in ambient noise, such as in a mobile setting (e.g., an emergency vehicle, on a hospital cart) or in a setting where many people (e.g., caregivers, patients, staff) may come and go. The "periodic" option, which is illustrated as being highlighted by highlight 70, may direct the pulse oximetry monitor 14 to monitor ambient sounds periodically, such as every 30 seconds, every minute, every two minutes, and so on. The periodicity of the ambient sounds monitoring may be user-defined or may be determined based upon the operational parameters of the pulse oximetry monitor 14. That is, a user may specify the amount of time between ambient noise sampling or a particular setting, such as while the pulse oximetry monitor 14 is on battery power, may determine the amount of time between sampling. The "periodic" option may be desirable in situations where the pulse oximetry monitor 14 is deployed in mobile settings, such that it is desirable to conserve battery power, or in settings where ambient sounds do not rapidly change. While in detection mode, the pulse oximetry monitor 14 may automatically generate a modified alarm in response to the continuous or periodic analysis of the ambient sounds.

In other embodiments, a user may desire to manually configure alarm settings. In such embodiments, returning to the display 20 illustrated in FIG. 2, a user may place the highlight 70 over the "MANUAL" mode. For example, the user may press the down arrow key 60 once to highlight the "MANUAL" mode, followed by selection using a "SELECT" or similar soft key 66. In such embodiments, the pulse oximetry monitor 14 may then display a manual mode screen 74, an embodiment of which is illustrated in FIG. 2B. In the illustrated embodiment, the user may select, via highlight 70, between an "adjust volume" option, an "adjust tone" option, an "input source" option, and a "learn new" option. As an example, in the "adjust volume" option, the user may adjust the volume of an original or any stored alarm such that the alarm has sufficient volume to allow the user to readily distinguish the alarm from ambient sounds. In the "adjust tone" option, the user may select and adjust one or more tones of an original or stored alarm, such as by viewing a frequency spectrum of an alarm and adjusting one or more frequencies accordingly. In such an option, the frequencies available for selection by the user may be limited by safety standards and so forth (e.g., I.E.C. 60601-1-8 standards), such that the user does not inadvertently select frequencies that would result in violation of the standard. Additionally or alternatively, the user may actively adjust an alarm, such as by listening to each tone sounded by the pulse oximetry monitor 14 and adjusting as appropriate. In the "input source" option, the user may select from a series of stored ambient sounds, such as those characteristic of a particular setting (e.g., a hospital or an emergency vehicle), and manually select an alarm from a list of stored alarms to sound in response to the selected ambient sounds. Similarly, in the "learn new" option, the user may define a set of ambient sounds (e.g., sounds characteristic of a particular setting) and select an appropriate alarm for the defined ambient sounds from a list of stored alarms.

Indeed, the pulse oximetry monitor 14 may be configured to sound a specific set of stored alarms in response to certain ambient sounds or based upon a user-defined setting. As an example, returning to the mode menu 54 illustrated in FIG. 2, the user may select the "PRE-CONFIGURED" mode by using the arrow keys 60 and soft keys 66 as described above. Further, in some configurations, actuation of the mode switch 28 may directly access the pre-configured mode, which allows the user to choose between options within the pre-configured menu. When the pre-configured mode is selected, the display 20 may then provide a pre-configured mode screen 76, an embodiment of which is illustrated in FIG. 2C. While in the pre-configured mode, the user may select between different settings in which the pulse oximetry monitor 14 is deployed for which the pulse oximetry monitor 14 has one or more pre-configured alarm responses. In the illustrated embodiment, the settings include an "ambulance" mode, a "helicopter" mode, a "hospital" mode, and a "stadium" mode. Indeed, based upon user input, for example while in "MANUAL" mode, other modes may be available that have been pre-configured for certain settings. In such embodiments, these modes would also be listed, such as by "user 1," "user 2," or "manual 1" or "manual 2." As noted above, the "ambulance" mode would direct the pulse oximetry monitor 14 to sound alarms that are not substantially masked by ambulance sounds, the "helicopter" mode (illustrated as highlighted by highlight 70) would direct the pulse oximetry monitor 14 to sound alarms that are not substantially masked by helicopter sounds, and so on. Each mode may specify a particular set of alarms, may direct the pulse oximetry monitor 14 to only monitor certain frequencies, may simply adjust volumes of alarms, or any combination of these.

Figure 2D:
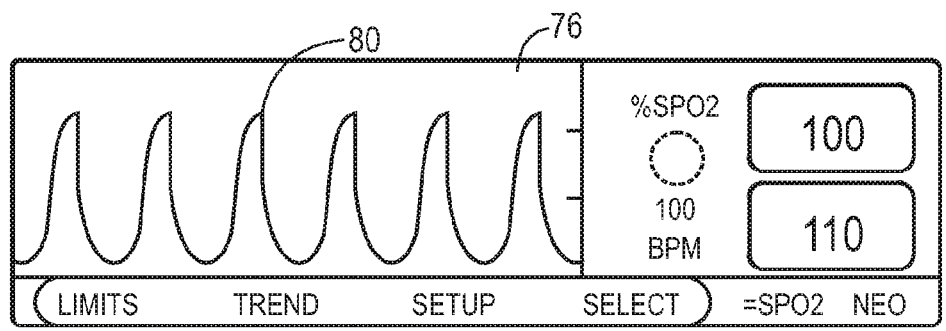
FIG. 2D is a front view of an embodiment of the pulse oximetry monitor of FIG. 2 after adjusting adaptive-alarm settings, in accordance with one aspect of the present technique.

After selecting a desired mode, making desired adjustments and so forth in accordance with the embodiments described above, the user may return to a main pulse oximetry screen 78, an embodiment of which is illustrated in FIG. 2D. Substantially real-time physiological information may be provided on the main pulse oximetry screen 78, for example as a plethysmographic waveform 80 or other related metric.

Returning to FIG. 2, in addition to the adaptive-alarm information provided on the display 20, the pulse oximetry monitor 14 may include various indicators 82 (e.g., indicator lights and display screen graphics) that facilitate operation of the pulse oximetry monitor 14 and observation of a patient's physiological metrics (e.g., pulse rate). In this way, even while the user is making adjustments to various settings, the user may also monitor the patient to which the pulse oximetry monitor 14 is connected and/or ascertain the status of the pulse oximetry monitor 14. Accordingly, some of the indicators 82 are specifically provided to facilitate monitoring of a patient's physiological parameters. For example, the indicators 82 may include representations of the most recently measured values for SpO$_2$, pulse rate, and pulse amplitude. Other indicators 82 may be specifically provided to facilitate operation of the pulse oximetry monitor 14. For example, the indicators 82 may include an A/C power indicator, a low battery indicator, an alarm silence indicator, a mode indicator, and so forth.

Figure 3:
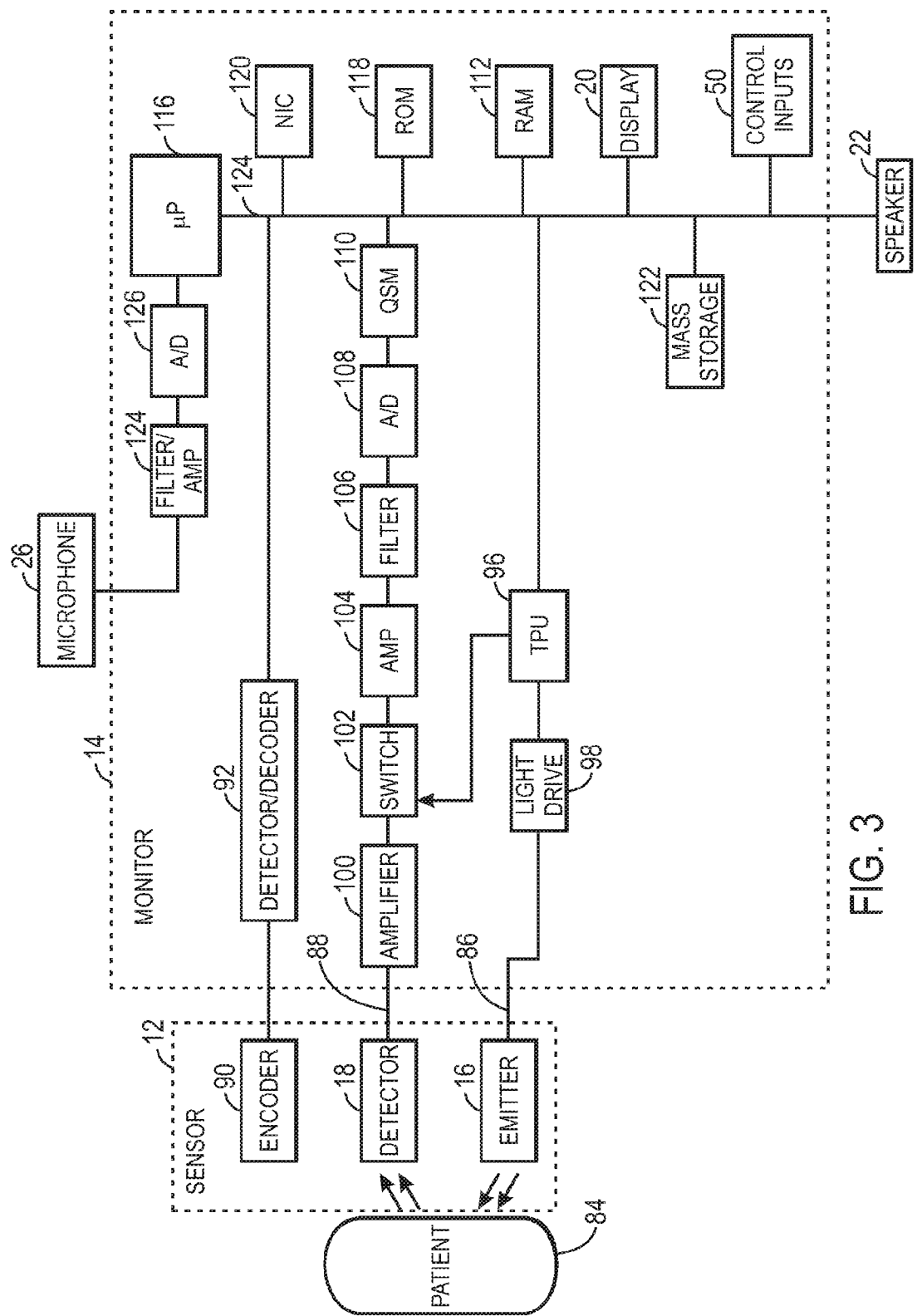
FIG. 3 is a block diagram illustrating the various components contained within the pulse oximetry monitor and sensor depicted in FIGS. 1 and 2, the pulse oximetry monitor having a microphone, processor, and related components of an adaptive alarm system, in accordance with an aspect of the present technique.

FIG. 3 is a block diagram of an embodiment of the pulse oximetry monitor 14 coupled to a patient 84 in accordance with present embodiments. As mentioned, embodiments of the pulse oximetry monitor 14 may be implemented with any suitable sensor and patient monitor, such as those available from Nellcor Puritan Bennett LLC. The pulse oximetry monitor 14 and the sensor 12, as discussed with respect to FIG. 1, may be configured to obtain, for example, a plethysmographic signal from patient tissue. The sensor 12, as noted above, includes the emitter 16 and detector 18. The sensor 12 further includes two cables, 86 and 88, which allow the sensor 12 to interface with the pulse oximetry monitor 14. The sensor 12 may also include an encoder 90, as described below. The cable 86 allows signals to be transmitted from the pulse oximetry monitor 14 to the emitter 16 and the cable 88 allows a signal to be transmitted from the detector 18 to the pulse oximetry monitor 14. The signals may be electrical signals or may be light signals (i.e., the cables 86, 88 may be electrical or fiber optic.) It should be noted that the cables 86, 88 may be contained within the cable 24 illustrated in FIG. 1.

The encoder 90 of the sensor 12 may contain information about the sensor 12, such as what type of sensor it is (e.g., whether the sensor is intended for placement on a forehead or digit), the wavelengths of light emitted by the emitter 12, and what features the sensor 12 may include, such as a built-in microphone. This information may allow the pulse oximetry monitor 14 to take appropriate action, such as the selection of appropriate algorithms, use of appropriate calibration coefficients, and so forth for calculating the patient's physiological parameters. The encoder 90 may, for instance, be a coded resistor whose value corresponds to the type of the sensor 12 and/or the wavelengths of light emitted by the emitter 16. These coded values may be communicated to a detector/decoder 92 disposed within the monitor 14, which determines how to calculate the patient's physiological parameters. In another embodiment, the encoder 90 may be a memory or may include memory circuitry on which one or more operational parameters may be stored for communication to the monitor 14. Indeed, in some embodiments, the encoder 90 may provide information to the monitor 14 indicating the sensor 12 includes a microphone, which may, in turn, set the monitor 14 into a certain mode, such as a detection mode. Such embodiments are described further with respect to FIG. 11. Examples of pulse oximetry sensors configured to cooperate with pulse oximetry monitors may include OxiMax® sensors available from Nellcor Puritan Bennett LLC.

To allow the pulse oximetry monitor 14 to generate the light for provision to the patient 84, a time processing unit (TPU) 96 may provide timing control signals to light drive circuitry 98. The light drive circuitry 98 may contain a set of emitters (e.g., LEDs) that may control which wavelength of light is emitted and may also control when light is emitted, and if multiple light sources are used, the multiplexed timing for the different light sources. Signals from the light drive circuitry 98 may be transmitted through cable 86 to the sensor 12 and may cause light to be sent out of the emitter 16 and into the patient tissue 84. The light may be absorbed and/or scattered by the tissue 84, and may be collected by the detector 18. The detector 18 may collect the light and send a representative signal to the pulse oximetry monitor 14 via the cable 88.

In a similar manner to the emission of light from the emitter 16, the gating-in of signals from the detector 18 to various processing circuitry within the pulse oximetry monitor 14 may be controlled by the TPU 96 through an amplifier 100 and a switching circuit 102. These signals may be sampled at the proper time, depending upon which of multiple light sources is illuminated, if multiple light sources are used. The received signals from the detector 18 may be passed through another amplifier 104, a low pass filter 106, and an analog-to-digital (A/D) converter 108 for amplifying, filtering, and digitizing the received signals. The digital data may then be stored in a queued serial module (QSM) 110, for later downloading to RAM 112 as the QSM 110 fills up.

The QSM 110 and RAM 112 may be connected to an internal bus 114, which allows various circuitry within the pulse oximetry monitor 14 to share and process information as appropriate. The raw digital diagnostic data stored in the QSM 110 and/or the RAM 112 may be further sampled by a microprocessor 116 of the pulse oximetry monitor 14. The microprocessor 116 may then generate specific diagnostic data of interest, such as pulse rate, blood oxygen saturation, and so forth to determine if an alarm condition exists. To generate such data of interest, the microprocessor 116 may calculate one or more physiological parameters of interest using various algorithms. These algorithms may utilize coefficients, which may be empirically determined, corresponding to, for example, the wavelengths of light used. In one embodiment, these algorithms may be stored in a ROM 118, which is attached to the internal bus 114.

Also attached to the internal bus 114 are the inputs 50, the display 20, and the speaker 22, which are described above with respect to FIGS. 1 and 2. The inputs 50, as described above, may include the mode switch 28 of FIGS. 1 and 2, the arrow keys 60 soft keys 66 of FIG. 2, as well as connection points for a keyboard, a mouse, a trackball, or similar input device. Additionally, a network interface card (NIC) 120 connected to the internal bus 114 allows a remote computer (e.g., the monitor 30 of FIG. 1) to provide and receive instructions, patient- and/or alarm-related information to and from the pulse oximetry monitor 14. Such information may be accessed via a mass storage 122, also connected to the internal bus 114, which may store caregiver preferences, patient information, or various parameters. Information such as programs for performing analyses on ambient sounds captured by the microphone 28 and for generating the alarms described above may also be stored on the mass storage 122, or may be stored on the ROM 118.

In addition to the acts related to light emission and detection for patient monitoring described above, the pulse oximetry monitor 14 may, substantially concurrently, perform adaptive-alarm-related tasks. Accordingly, the mass storage 122 and/or other storage circuitry such as the RAM 112 and/or ROM 118 may store information and algorithms related to tasks such as alarm generation on the fly (new alarm generation), original alarm modification, selection of a pre-generated alarm, and user-configured alarms. However, as noted above, before performing such alarm generation/modification, the pulse oximetry monitor 14 first performs analysis of the ambient sounds to determine if modified alarm generation is appropriate.

In performing the analysis, the pulse oximetry monitor 14 captures ambient sounds with the microphone 28 and analyzes the ambient sounds with the microprocessor 116. Specifically, the microphone 28 may act as a transducer to capture ambient sounds and generate a signal representative of the ambient sounds. The representative signal may be filtered and amplified by a filter/amp 124. In some embodiments, the filter/amp 124 may filter signals representative of sounds outside of the average range of perception by humans. In one embodiment, the filter/amp 124 may filter out (remove) signals representative of frequencies outside of the range between approximately 20 Hz and 20000 Hz, approximately 510 Hz and 16000 Hz, or approximately 1000 Hz and 12000 Hz. In one embodiment, the filter/amp 124 may remove all frequencies outside of the range of the original alarms sounded by the pulse oximetry monitor 14, such that substantially only those frequencies that may potentially mask the original alarms are analyzed. The filtered signal may then be converted from analog to digital by an analog-to-digital (A/D) converter 126, which sends a digital signal representative of the ambient sounds to the microprocessor 116 for analysis. In filtering the ambient sounds signal, the microprocessor 116 may perform the analysis between the ambient sounds and the stored and/or original alarms more efficiently, as the number of frequencies that are analyzed has been limited. This may allow lower processing power to be used for performing the FFT that generates a frequency spectrum of the ambient sounds. Accordingly, the microprocessor 116 may be a microprocessor with lower processing power than would otherwise be suitable if filtering were not performed. Nevertheless, the microprocessor 116 then performs the analysis between the ambient sounds signal and the original alarms stored by the pulse oximetry monitor 14. For example, the microprocessor 116 may access spectrum analyzer software stored on the mass storage 122 and/or RAM 112 to compare frequency spectra of ambient sounds to the frequency spectra of one or more original alarms to determine whether modified alarm generation is appropriate. When the ambient sounds are determined to not have a substantial effect on the original alarms, the original alarms may be sounded by the speaker 22 upon detection of the presence of an alarm condition. In embodiments where the microprocessor 116 determines that modified alarm generation is appropriate, algorithms stored on the memory circuitry (e.g., the mass storage 122, the RAM 112 and/or the ROM 118) are performed to generate an alarm on the fly (new alarm generation), modify an original alarm, select a pre-generated alarm, or to allow a user to manually configure an alarm. The alarm so generated may then be sounded by the speaker 22.

To generate one or more alarms on the fly, such as in the detection mode described above with respect to FIG. 2, the microprocessor 116 may run an algorithm stored on the mass storage 122 (or other memory circuitry) that is capable of determining frequencies that are not masked by ambient sounds (i.e., available frequencies). Further, the volume of each ambient sound frequency (or filtered frequency) may be analyzed by one or more algorithms, such that the volume of the alarm generated on the fly is at an appropriate volume. The microprocessor 116 may then run one or more sound synthesis algorithms to string together two or more of the available frequencies to generate an alarm. The microprocessor 116 may also run one or more stored algorithms that are capable of forming ambient sounds trends, such that alarms generated on the fly may be stored for later use when similar or the same ambient sounds are encountered.

In some embodiments, generating an alarm on the fly may result in a new alarm altogether. However, it may be desirable to generate a modified alarm that substantially retains the essence of an original alarm while suitably adjusting the original alarm (e.g., by tone, pitch, volume) to account for the ambient sounds. Such a modified alarm may be desirable in embodiments where the pulse oximetry monitor 14 monitors more than one parameter and contains more than one concomitant alarm. Therefore, the microprocessor 116 may access the mass storage 122 and/or RAM 112, which may store the original alarm that corresponds to pulse rate, blood oxygen saturation, and total hemoglobin, among others, as well as their representative frequency spectra. The microprocessor 116 may then execute one or more algorithms stored on the mass storage 122 and/or the RAM 112 for modifying the tone, pitch, and/or volume of one or more of the frequencies of the original alarms.

In addition to the original alarms that may be modified, the mass storage 122 and/or the RAM 112 may also store several pre-generated alarms as well as their representative frequency spectra, for example to use in lieu of the original alarms where appropriate. For example, in the pre-configured mode described above, when the user selects a mode such as the "ambulance mode," the microprocessor 116 may run one or more algorithms that override the use of the original alarms and selects one or more ambulance-appropriate pre-generated alarms stored on the mass storage 122 and/or RAM 112. In other embodiments, the microprocessor 116 may, when a modified alarm is deemed appropriate, run analysis algorithms to compare the ambient sounds spectra to the pre-generated alarms spectra. The microprocessor 116 may then select a pre-generated alarm that is not substantially masked by or appropriately distinguishes over the ambient sounds.

In addition to or in lieu of allowing the pulse oximetry monitor 14 to automatically generate and/or select an alarm as described above, a user may manually configure one or more alarms of the pulse oximetry monitor 14, such as when in the manual mode. To facilitate such configuration and personalization, the mass storage 122 and/or RAM 112 may store historical data, configuration and personalization options, frequency spectra, and so forth. For example, the mass storage 122 and/or RAM 112 may store historical data relating to various ambient sounds in a given setting which allows a user to program a certain response (i.e., a stored alarm or a manually-configured alarm) to utilize when such ambient sounds are again encountered. The user may access such data and settings options using the inputs 50 and the display 20 to configure alarms (i.e., create new alarms, modify tones, pitches, and volumes of original alarms) as desired.

It should be noted that the acts and methods introduced above may be performed by one or more processing components, such as the microprocessor 116, substantially automatically or along with user input. That is, in one embodiment, some of the methods introduced above and described in further detail below may be partially or fully implemented on software, which may allow for a re-configuration of a conventional patient monitor to perform these adaptive alarm tasks. For example, spectral analysis may be performed by suitably configured software that is readily available and stored on the memory circuitry within the pulse oximetry monitor 14. Further, the pulse oximetry monitor 14 may be modified to include or may be connected to another piece of equipment including the speaker 22 and/or the microphone 26. Therefore, the methods introduced above may be applicable to newly manufactured medical devices or medical devices that have been outfitted with adaptive-alarm capability.

Figure 4:
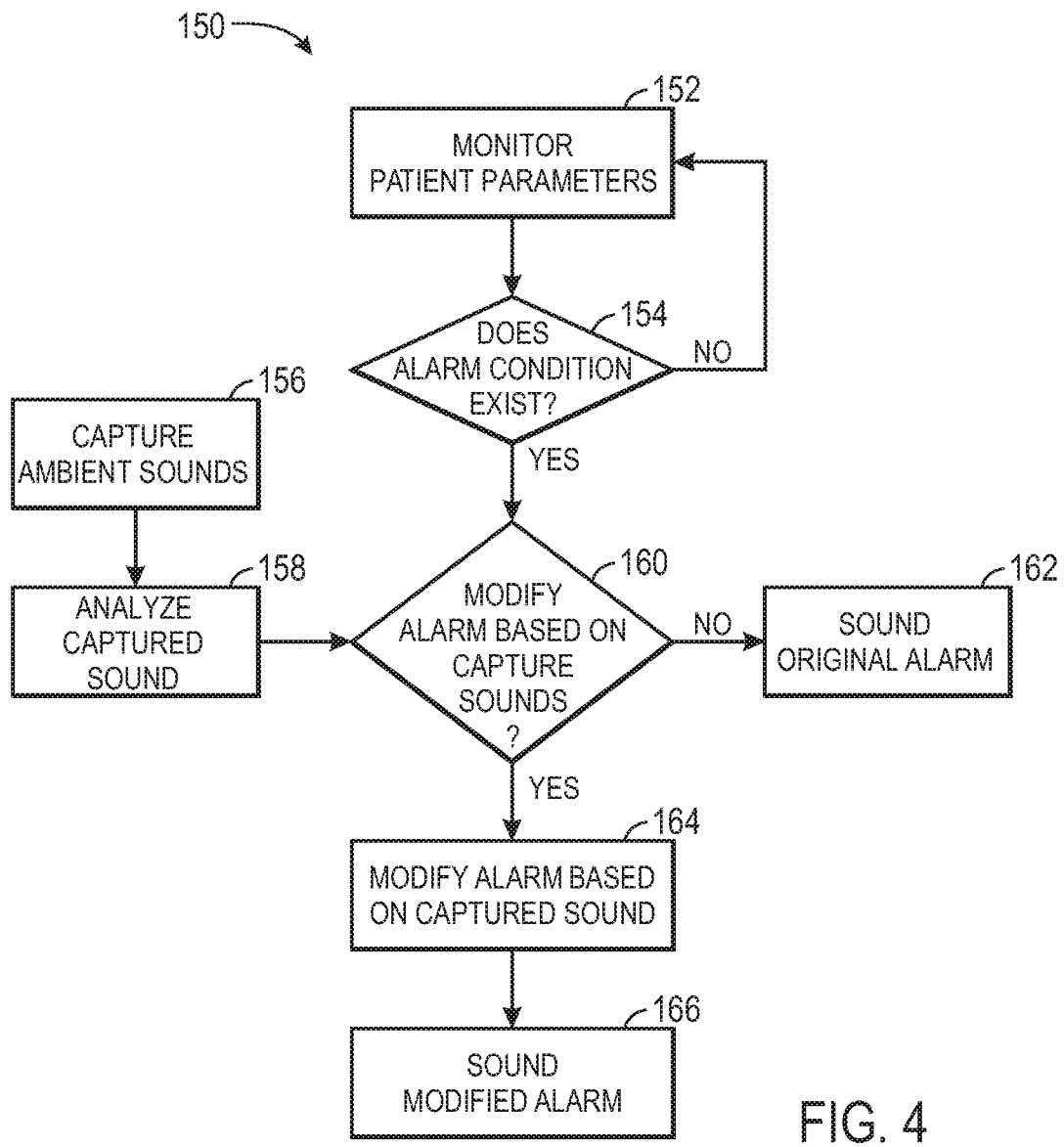
FIG. 4 is a flow chart illustrating an embodiment of a method of monitoring a patient and generating a modified alarm where appropriate using the pulse oximetry monitor illustrated in FIGS. 1-3, in accordance with an aspect of the present technique.

FIG. 4 illustrates a high-level flow chart depicting an example of one such method 150 in which the pulse oximetry monitor 14 monitors the patient and generates an original or modified alarm. When a modified alarm is generated, the modification may be frequency-based and/or volume-based, which will be described below with respect to FIGS. 7-10. As noted above, the pulse oximetry monitor 14 may monitor patient physiological parameters (block 152). The pulse oximetry monitor 14 may compare the monitored physiological parameters from block 152 to a set of stored predefined data values which, where appropriate, signals to the pulse oximetry monitor 14 whether an alarm condition may exist. Accordingly, the pulse oximetry monitor 14 may substantially continuously determine if an alarm condition exists (query 154) based on the measured patient parameters.

While the pulse oximetry monitor 14 substantially continuously determines if an alarm condition exists (query 154), the pulse oximetry monitor 14 may also capture ambient sounds (block 156). For example, as noted above, the microphone 26 (or the speaker 22) may capture ambient sounds so that a signal representative of the ambient sounds may be provided to the microprocessor 116 (FIG. 3) for analysis (block 158). In embodiments where an alarm condition does not exist, the method 150 may cycle back to monitoring patient parameters (block 152) and the pulse oximetry monitor 14 may continue to substantially simultaneously capture ambient sounds (block 156) and perform analyses on the same (block 158).

It should be noted that by performing such analyses (block 158) and determinations (query 154) substantially concurrently, in embodiments where an alarm condition is identified (such as when measured patient parameters have dropped below or exceeded threshold values), the pulse oximetry monitor 14 may promptly perform a follow-up determination as to whether the alarm corresponding to the alarm condition should be modified (query 160). In embodiments where the pulse oximetry monitor 14 determines that no modified alarm is needed, the pulse oximetry monitor 14 may sound the original alarm (block 162) corresponding to the alarm condition. However, in embodiments where the pulse oximetry monitor 14 determines that a modified alarm is needed, the pulse oximetry monitor 14 may generate a modified alarm based on the captured ambient sounds (block 164). For example, the pulse oximetry monitor 14 may synthesize a new alarm on the fly, may modify the original alarm (including modifying the volume, the pitch, the tone, etc.), or may select a pre-generated alarm from a table. Nevertheless, the nature of the modified alarm may be a direct result of the analysis of the captured ambient sounds (block 158), such that the new or modified alarm is substantially free of masking by the ambient sounds. Accordingly, the pulse oximetry monitor 14 may sound the modified alarm (block 166) to alert the caregiver that an alarm condition exists.

Figure 5:
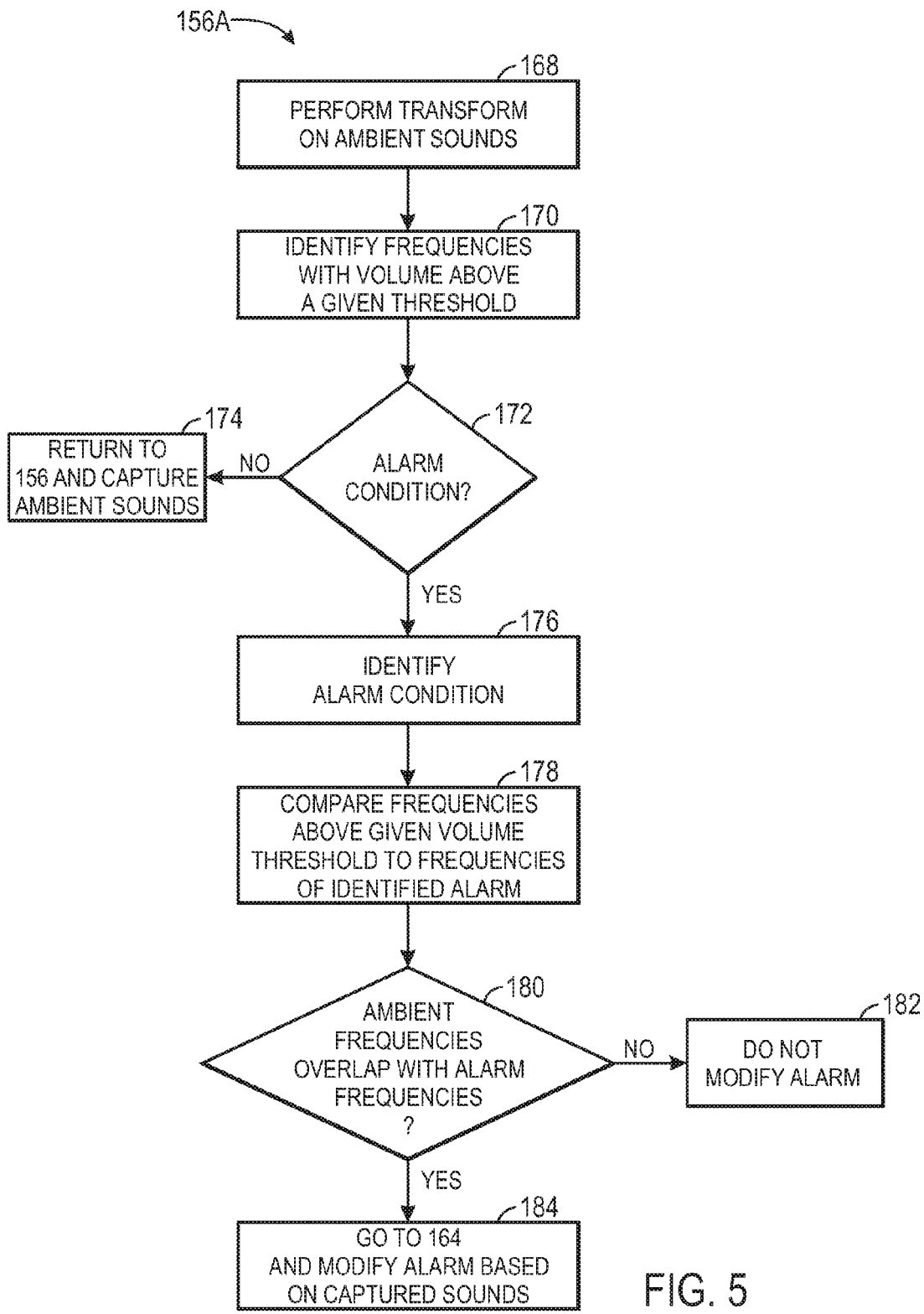
FIG. 5 is a flow chart illustrating one embodiment of a method of analyzing captured ambient sounds and alarm generation determination using the pulse oximetry monitor of FIGS. 1-3, in accordance with an aspect of the present technique.

To allow the pulse oximetry monitor 14 to perform frequency adjustment to generate a modified alarm, the present techniques provide a method 156A for analyzing the frequencies of captured sounds and comparing them to frequencies of stored original alarms, which is illustrated as a flow chart in FIG. 5. Upon capturing the ambient sounds (block 156, FIG. 4), a transform may be performed on a signal representative of the ambient sounds (block 168), which results in a frequency spectrum of the ambient sounds. In some embodiments, the transform may be a Fast Fourier Transform (FFT), a discrete Fourier Transform (DFT), or any similar transform. Accordingly, the pulse oximetry monitor 14 may act as a digital or hybrid analog-digital spectrum analyzer, which transforms the captured ambient sounds into the components of its frequency spectrum. In one embodiment, the pulse oximetry monitor 14 may perform the analysis in substantially real-time (i.e., less than approximately 5 seconds).

While the pulse oximetry monitor 14 may be capable of analyzing the full frequency spectrum of the captured ambient sounds, it should be noted that not every frequency of the ambient sounds may mask an alarm. Therefore, a threshold may be set (e.g., by a user or automatically by the pulse oximetry monitor 14) to exclude frequencies having sufficiently low volume (e.g., amplitude, intensity, power) so as not to interfere with original alarm frequencies and to focus on frequencies that have sufficient volume to mask original alarm frequencies. Accordingly, the pulse oximetry monitor 14 may identify frequencies having volumes above the threshold (block 170). As an example of possible thresholds, the frequency spectrum may be a plot of frequency versus amplitude, frequency versus decibel level (dB), frequency versus intensity, and so forth, each of which may have a threshold value. In some embodiments, volume, as measured by the amplitude, dB level, intensity, or power, may be a perceived quality of the ambient sounds (i.e., may differ between users). As such, adaptive-alarm settings, such as volume thresholds, of the pulse oximetry monitor 14 may be customized for each caregiver.

After identifying one or more frequencies having a volume above a certain threshold (block 170), the pulse oximetry monitor 14 then determines if an alarm condition exists (query 172), which may or may not correspond to the query 154 of FIG. 4. In situations where an alarm condition does not exist, the pulse oximetry monitor 14 will return to the capturing ambient sounds block 156 in FIG. 4 (block 174). If an alarm condition does exist, the type of alarm condition is then identified (block 176). For example, if the pulse oximetry monitor 14 is configured to monitor more than one patient parameter (pulse rate, blood oxygen saturation, total hemoglobin, etc.), the type of alarm may be identified, as each alarm corresponding to each metric may be different. In one embodiment, each physiological metric may have a corresponding alarm, such that a caregiver may recognize the type of alarm even when the pulse oximetry monitor 14 is not within sight. Therefore, each alarm may have a distinct and characteristic quality of tone and pitch/perceived pitch, with different component frequencies.

Upon identification of the alarm condition (block 176), the pulse oximetry monitor 14 may then compare the frequencies of the identified alarm with the frequencies of the ambient sounds above the given threshold (block 178). For example, the pulse oximetry monitor 14 may perform a matching function to determine if the frequencies of the ambient sounds overlap with those of the identified original alarm. The extent of overlap between the ambient sounds and the identified original alarm may determine whether the identified original alarm may be masked by the ambient sounds (query 180). As an example, the alarm may be at least partially masked if the degree of frequency overlap is at least approximately 20%. In the event that there is not substantial overlap between the ambient sounds and the identified original alarm, the pulse oximetry monitor 14 may not modify the alarm (block 182). In embodiments where there is substantial overlap between the frequencies of the ambient sounds and the identified original alarm, such as when the percentage overlap meets, exceeds, or falls within a predetermined range, the pulse oximetry monitor 14 may then modify the original alarm based on the captured ambient sounds (block 184). Indeed, the query 180 may correspond, at least in part, to the query 160 of FIG. 4. Similarly, block 184 may correspond, at least in part, to block 164 of FIG. 4.

Figure 6:
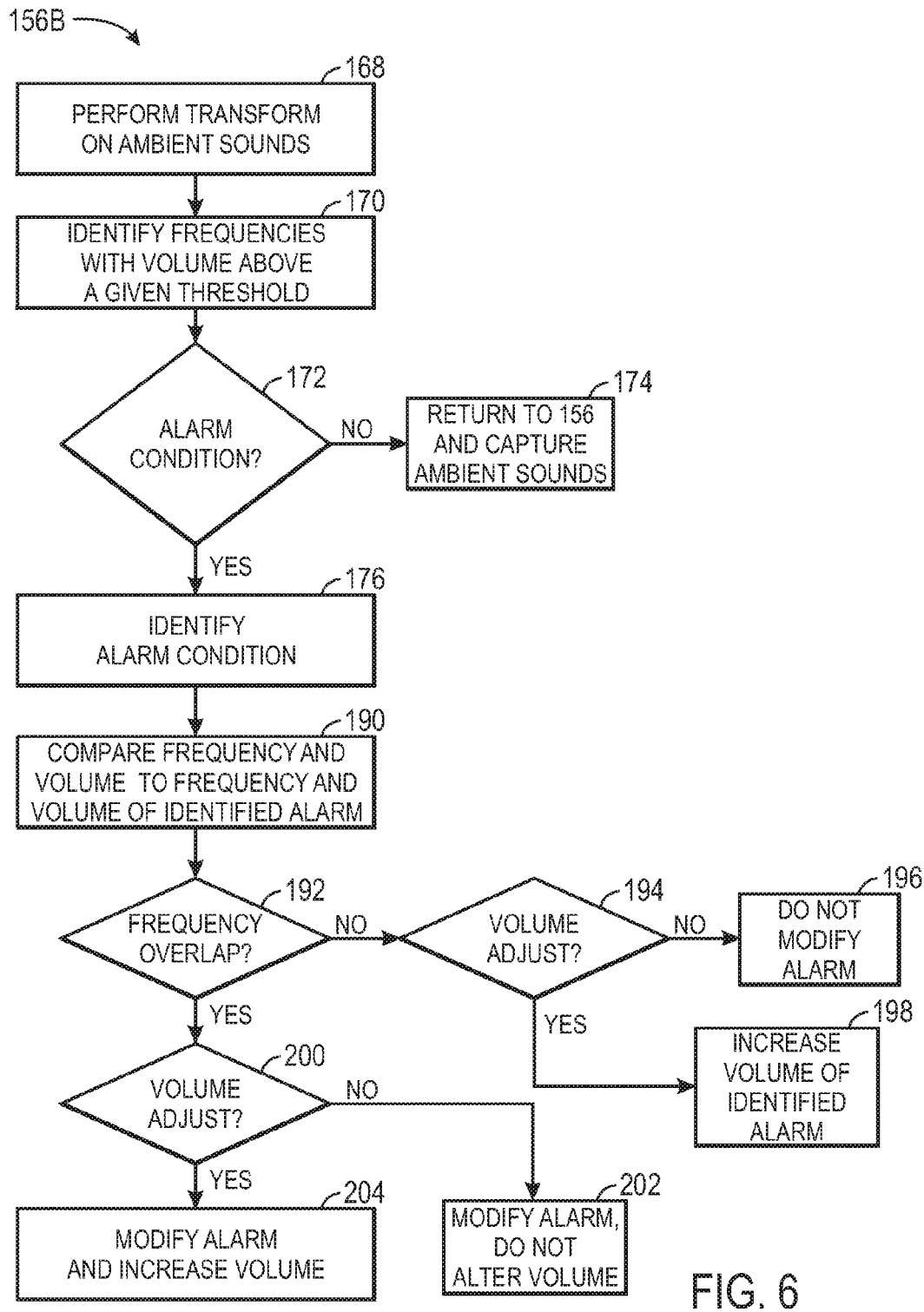
FIG. 6 is a flow chart illustrating another embodiment of a method of analyzing captured ambient sounds and alarm generation determination which accounts for volume using the pulse oximetry monitor of FIGS. 1-3, in accordance with an aspect of the present technique.

It should be noted that an original alarm may be masked even in situations where there is little to no overlap of frequencies between the original alarm and ambient sounds, such as when the ambient sounds are sufficiently loud (i.e., have sufficient volume) to drown out the original alarm. Therefore, in addition to the frequency analysis described above, the pulse oximetry monitor 14 may also analyze the volume (i.e., dB level, intensity, power, amplitude) corresponding to the frequencies and compare the volume to the volume of the original alarm, such that volume adjustment in addition to or in lieu of frequency adjustment may be performed. FIG. 6 is a flow chart illustration of one such method 156B of analyzing the frequencies of the captured ambient sounds and their volumes, and determining whether a modified alarm should be volume and/or frequency-adjusted.

The initial frequency analysis acts performed by the pulse oximetry monitor 14 in method 156B may be similar or the same to those of method 156A. Accordingly, those steps are referred using the same reference numerals. The initial frequency analysis includes performing a transform (e.g., FFT, FT, DFT) on the ambient sounds signal (block 168), identifying frequencies with a volume above a given threshold (block 170), determining if an alarm condition exists (query 172), and identification of the alarm condition (block 176). Of course, if an alarm condition does not exist, the method returns to block 156 of FIG. 4 to capture ambient sounds (block 174).

Upon identification of the alarm condition (block 176), the pulse oximetry monitor 14 may then compare the frequencies of the ambient sounds that are above a given volume threshold with the frequencies and their volumes corresponding to the identified original alarm (block 190). That is, the pulse oximetry monitor 14 may compare various measurements relating to volume between the ambient sounds and the identified original alarm. Such measurements may include the amplitudes of the frequencies (e.g., peak, root mean square (RMS), pulse, instantaneous), the dB level of the frequencies, the RMS amplitude for the overall ambient sounds signal, and the like.

The volume and frequency comparisons described above may allow the pulse oximetry monitor 14 to determine if substantial frequency overlap and/or volume levels exist such that the identified original alarm may be masked. In the illustrated embodiment, the pulse oximetry monitor 14 determines whether there is substantial overlap between the frequencies of the ambient sounds and those of the identified original alarm (query 192). As noted above, substantial overlap may be present if the degree of frequency overlap is at least approximately 20%. Ultimately, the query 192 may determine whether the frequencies of the original alarm are modified. However, it should be noted that a determination as to whether the volume of the generated alarm should be modified may be performed regardless of the degree of frequency overlap between the ambient sounds and the original alarm.

In embodiments where there is not a substantial overlap of frequencies, the pulse oximetry monitor 14 then determines if the identified original alarm may benefit from volume adjustment (query 194). In situations where the ambient sounds are not sufficiently loud to mask the identified original alarm, the pulse oximetry monitor 14 may not modify the identified alarm (block 196) and sound the original alarm. In situations where the ambient sounds are sufficiently loud to mask the identified original alarm, the pulse oximetry monitor 14 may increase the volume of the identified original alarm (block 198) to a level where a user may clearly recognize the original alarm, even in the presence of the ambient sounds. It should be noted that the volume increase may be to a level where the average volume measurement value of the identified original alarm is at least approximately 20% greater than the highest volume measurement value of the ambient sounds. For example, the average volume measurement value of the identified alarm may be increased to at least approximately 10% greater than the highest value for the ambient sounds.

In embodiments where there is a substantial overlap of frequencies between the ambient sounds and the identified alarm, the pulse oximetry monitor 14 then makes a determination as to whether the modified alarm will benefit from a volume adjustment (query 200). In embodiments where the ambient sounds are not sufficiently loud to mask the modified alarm, the modified alarm will not be volume-adjusted (block 202). In situations where the ambient sounds have a high measured volume, the alarm may be volume-adjusted (block 204). As with the volume modification of the identified original alarm (block 198), the modified alarm's average volume measurement value may be increased to at least 10% greater than the highest value of the same for the ambient sounds (block 204).

Figure 7:
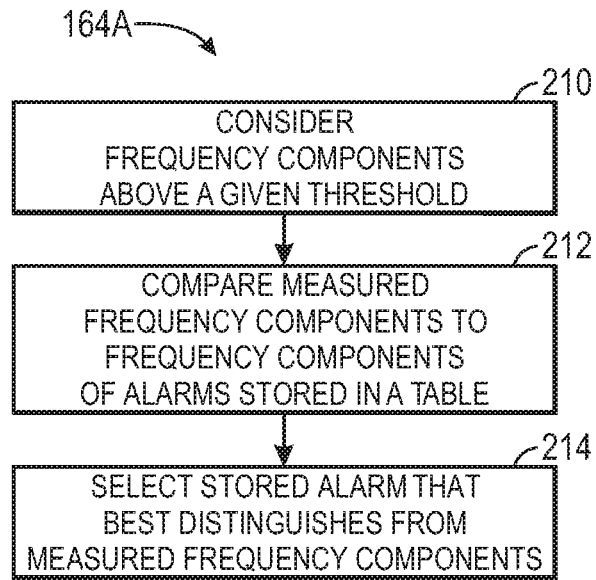
FIG. 7 is a flow chart illustrating one embodiment of a method of generating an alarm by allowing the pulse oximetry monitor of FIGS. 1-3 to select an appropriate alarm from a list of stored alarms, in accordance with an aspect of the present technique.
Figure 8:
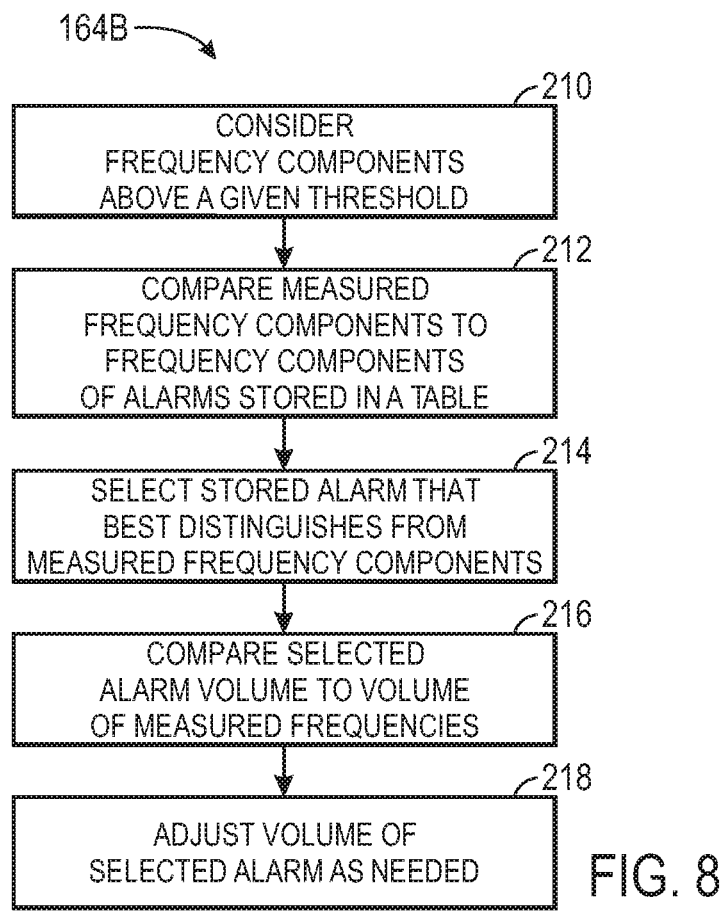
FIG. 8 is a flow chart illustrating one embodiment of a method of generating an alarm by allowing the pulse oximetry monitor of FIGS. 1-3 to select an appropriate alarm from a list of stored alarms and to adjust a volume of the selected alarm, in accordance with an aspect of the present technique.
Figure 9:
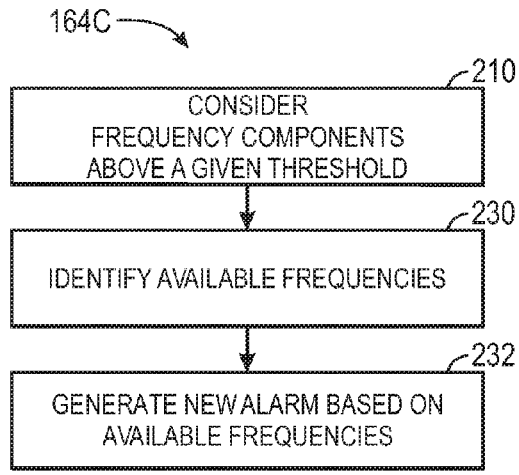
FIG. 9 is a flow chart illustrating one embodiment of a method of generating an alarm on the fly by identifying and selecting available frequencies using the pulse oximetry monitor of FIGS. 1-3, in accordance with an aspect of the present technique.
Figure 10:
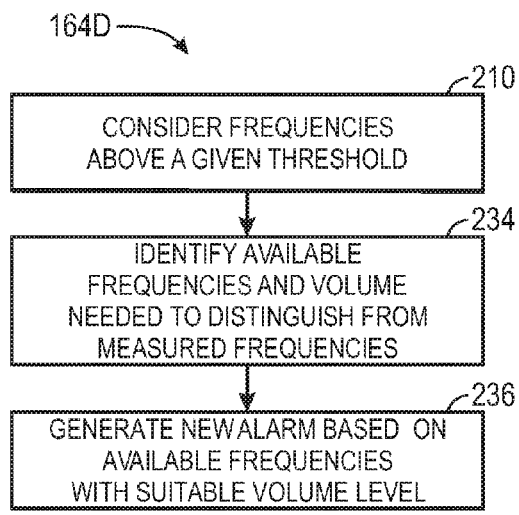
FIG. 10 is a flow chart illustrating one embodiment of a method of generating an alarm on the fly by identifying and selecting available frequencies and adjusting volumes of the selected frequencies using the pulse oximetry monitor of FIGS. 1-3, in accordance with an aspect of the present technique.

Once the pulse oximetry monitor 14 has performed analysis of the ambient sounds according to either of the methods described above in FIGS. 5 and 6, the pulse oximetry monitor 14 then, as noted above in FIG. 4, generates a modified alarm based on the captured ambient sounds in block 164. The modification may include selecting a pre-generated alarm from a table or modifying an original alarm by adjusting frequency and/or volume to slightly modify the original alarm or to generate a new alarm altogether. Such methods are discussed in the context of flowcharts illustrated in FIGS. 7-10. Specifically, FIG. 7 is a flow chart depicting one method 164A of alarm generation that includes selecting an alarm from a list of pre-generated alarms stored in a table. FIG. 8 is a flow chart depicting a method 164B of alarm generation that is similar to the method 164A, and includes volume adjustment of the alarm. Methods 164A and 164B may be implemented, for example, in situations where the response of the pulse oximetry monitor 14 (i.e., the sounding of a modified alarm) is desired in a short timeframe or when the pulse oximetry monitor 14 is placed in a setting-specific mode, such as an ambulance mode. FIG. 9 is a flow chart depicting a method 164C of generating a modified alarm by adjusting frequencies with respect to the captured ambient sounds, and FIG. 10 is a flow chart depicting a similar method 164D that includes volume adjustment in addition to frequency adjustment. Methods 164C and 164D may be applicable to generating an alarm on the fly, such as generation of a new alarm or modification of an original alarm.

Referring now to FIG. 7, the method 164A, as noted above, includes the selection of an appropriate stored alarm from a table in response to the analysis of the ambient sounds performed by the pulse oximetry monitor 14. To concentrate on only those frequencies of the ambient sounds that may mask an original alarm, the pulse oximetry monitor 14 may consider the frequencies of the ambient sounds that meet or exceed a pre-defined threshold volume (block 210) as described above. The considered frequencies of the ambient sounds are then compared to frequency components (within frequency spectra) of alarms stored in the pulse oximetry monitor 14 (block 212). As an example, the pulse oximetry monitor 14 may perform a frequency matching or mapping function that determines the amount of frequency overlap between the ambient sounds and the stored alarms. The stored alarm that best distinguishes from the measured frequency components of the ambient sounds is then selected (block 214). For example, the pulse oximetry monitor 14 may designate a percentage match for each of the alarms with regard to the measured frequencies of the ambient sounds. The percentage match may represent the percentage of frequencies in the stored alarm that overlap with frequencies of the ambient sounds. In such embodiments, the pulse oximetry monitor 14 may select an alarm with the lowest percentage match.

To account for situations where the ambient sounds have sufficient volume to mask a selected alarm regardless of frequency differences, the pulse oximetry monitor 14 may perform the method 164B, which, as noted above, contains similar acts to those described above with respect to method 164A and includes selecting a stored alarm and subsequently (or substantially concurrently) performing volume adjustment. Method 164B includes nearly identical initial steps to those of method 164A. Accordingly, method 164B includes block 210, block 212, and block 214, which are described above. After the modified alarm has been selected (block 214), a volume of the modified alarm is compared to a volume of the ambient sounds (block 216) in a similar manner to that described above with respect to FIG. 6. In embodiments where the volume of the ambient sounds indicates that the modified alarm may be masked, the pulse oximetry monitor 14 may increase the volume of the selected alarm (block 218). For example, the modified alarm's volume may be increased to at least approximately 10% greater than the highest and/or average volume measurement of the ambient sounds. To perform such volume modification, the pulse oximetry monitor 14 may adjust the amplitude of the frequencies of the modified alarm.

While the methods 164A and 164B described above may be applicable when the pulse oximetry monitor 14 is in a setting-specific mode, such as the ambulance, helicopter, hospital, or similar pre-configured mode, the pulse oximetry monitor 14 may instead perform methods 164C and 164D described below when set to a different mode, such as the detection mode described above with respect to FIG. 2. For example, it may be desirable to modify an original alarm's pitch and/or tone, or to generate a new alarm altogether. That is, the pulse oximetry monitor 14 may, in certain embodiments, synthesize a modified alarm on the fly. The modified alarm may be synthesized either de novo or may be based upon the essence of the existing tones of the original alarm identified in block 176 of FIG. 5. As noted above, FIGS. 9 and 10 illustrate such methods 164C and 164D for synthesizing a modified alarm on the fly.

According to the method 164C depicted in FIG. 9, the pulse oximetry monitor 14 may identify available frequencies and generate a modified alarm based on the same. As with the methods 164A and 164B described above, the pulse oximetry monitor 14 may consider the frequency components of the ambient sounds that meet or exceed a given threshold (block 210), such as a volume threshold. Based upon an analysis of the frequency components of the ambient sounds, frequencies are identified where the ambient sounds do not emit, or do not emit at a predefined volume (block 230). The pulse oximetry monitor 14 may then generate a modified alarm based on the available frequencies (block 232). For example, based on the identified available frequencies, the identified original alarm may be modified, such as by shifting a masked frequency of a beep tone to an available frequency. In other embodiments, a new alarm may be synthesized de novo, where the alarm does not substantially retain the essence of the identified original alarm.

To modify the original alarm, the pulse oximetry monitor 14 may change the pitch or perceived pitch of at least one of the beep tones of the original alarm. For example, the pulse oximetry monitor 14 may add overtones, such as partial overtones, harmonic overtones, and so forth to one or more of the beep tones. In this way, the pulse oximetry monitor 14 retains the essence of the original alarm while distinguishing (unmasking) it from the ambient sounds. Additionally or alternatively, the pulse oximetry monitor 14 may modify the original alarm by increasing the frequency of at least one or a combination of the beep tones by one or more octaves, such that the alarm's essence is substantially retained.

In embodiments where the modified alarm is generated de novo, the pulse oximetry monitor 14 may select one or more frequencies that are substantially free of masking by the ambient sounds. The pulse oximetry monitor 14 may then string together a series of tones having such frequencies to generate the modified alarm. To allow a caregiver to recognize the nature of the modified alarm that has been generated de novo, the pulse oximetry monitor 14 may retain one or more properties of the original alarm, such as the number of beep tones. As an example, an original alarm with three tones may correspond to a blood oxygen saturation alarm while an original alarm with two tones may correspond to a pulse alarm, and so on. In such embodiments, a caregiver may recognize that a modified alarm having three tones corresponds to the blood oxygen saturation alarm and that a modified alarm having two tones corresponds to the pulse alarm.

Indeed, in generating a modified alarm de novo, any combination of tones may be used, such that the modified alarms comply with I.E.C. 60601-1-8 standards.

In addition to the frequency-related on the fly modified alarm generation acts described above, the pulse oximetry monitor 14 may be configured to determine a suitable volume level for the modified alarm, such that its tones are not overwhelmed by the ambient sounds. FIG. 10 is a flow chart illustration depicting one such method 164D that determines a suitable volume of a modified alarm generated on the fly. As with the methods described above, the pulse oximetry monitor 14 may consider frequencies above a given threshold, such as a volume threshold (block 210). Subsequently, in addition to identifying which frequencies are available (i.e., not present within a frequency spectrum of the ambient sounds), the pulse oximetry monitor 14 may determine a suitable volume (as defined by a volume measurement) such that the modified alarm generated on the fly may be recognizable even in the presence of loud ambient sounds (block 234). Therefore, the pulse oximetry monitor 14 may use the volume of the frequencies of the ambient sounds to determine a suitable volume for the frequencies that are selected. The pulse oximetry monitor 14 may then synthesize the modified alarm based on the available frequencies, with the generated frequencies having a volume level suitable for recognition (block 236). When the modified alarm is a modified original alarm, such as when one or more beep tones have been modified but the alarm retains its essence, the pulse oximetry monitor 14 may modify the volume of its frequencies, as described above with respect to FIG. 8.

As noted above, the methods disclosed herein performed by the pulse oximetry monitor 14 may utilize ambient sounds that are captured via a transducer (i.e., a microphone or a suitably configured speaker). Further, the methods disclosed herein may be performed on a newly manufactured pulse oximetry monitor having a built-in speaker, or may be performed on an existing pulse oximetry monitor having suitably configured software. In such embodiments, it may be desirable to provide an external microphone that is capable of being coupled to the pulse oximetry monitor 14 for capturing ambient sounds. It should be noted that existing pulse oximetry monitors may not have a dedicated interface for coupling with a microphone. However, the present techniques may provide for the pulse oximetry sensor 12 to have a built-in microphone, such that the pulse oximetry sensor 12 may collect the ambient sounds and provide a signal representative of the ambient sounds to the processing components within the monitor 14 through the sensor interface 52 (FIG. 2). One such embodiment of the pulse oximetry sensor 12 is illustrated in FIG. 11, which is a perspective view of the pulse oximetry sensor 12 having the microphone 26.

Figure 11:
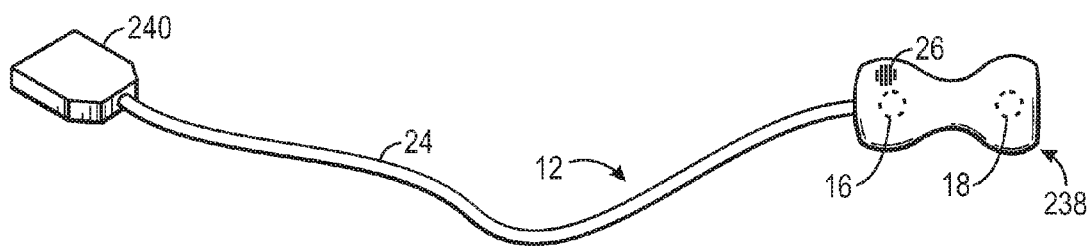
FIG. 11 is an illustration of an embodiment of the pulse oximetry sensor of FIGS. 1 and 2 having a built-in microphone for capturing ambient sounds, in accordance with an aspect of the present technique.

Specifically, the pulse oximetry sensor 12 of FIG. 11 includes the emitter 16, detector 18, and the microphone 26 in a main sensor body 238. It should be noted that the main sensor body 238 may also include the encoder 90 described above with respect to FIG. 2, which may be memory circuitry that is capable of providing information about the pulse oximetry sensor 12 to the pulse oximetry monitor 14. The pulse oximetry sensor 12 also includes a connector 240 coupled to the main sensor body 238 via the cable 24. The connector 240 enables the ambient sounds collected by the microphone 26 as well as the physiological data generated by the emitter 16 and detector 18 to be provided to the pulse oximetry monitor 14 through connection with the sensor interface 52 (FIG. 2). Further, as noted above, after connecting the pulse oximetry sensor 12 with the pulse oximetry monitor 14, the information stored on the pulse oximetry sensor 12 may place the pulse oximetry monitor 14 into the detection mode described above, where the pulse oximetry monitor 14 periodically or substantially continuously performs acoustic analysis of ambient sounds captured by the microphone 26.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A patient monitor, comprising:
a processor configured to generate a default alarm signal in response to patient physiological data indicative of an alarm condition, and configured to modify the default alarm signal to generate a new alarm signal in response to an ambient sounds input and patient physiological data indicative of the alarm condition, wherein the new alarm signal comprises a different frequency such that the new alarm signal has a different tone and/or pitch compared to the default alarm signal; and
a user interface coupled to the processor and being operable to receive the new alarm signal generated by the processor and to provide a user-audible indication of the alarm condition, the user-audible indication being masked less by ambient sounds in an environment in which the patient monitor is located compared to the default alarm signal.

2. The patient monitor of claim 1, comprising a second user interface coupled to the processor being operable to allow a user to provide the ambient sounds input to the processor for generating the new alarm signal.

3. The patient monitor of claim 1, wherein the processor is configured to perform an acoustic analysis of ambient sounds and to generate the new alarm signal in response to the analysis.

4. The patient monitor of claim 3, wherein the acoustic analysis comprises a comparison of frequencies of the ambient sounds to frequencies of the default alarm signal, and wherein the processor is configured to generate the new alarm signal having different frequencies than the frequencies of the ambient sounds if the frequencies of the default alarm signal and the ambient sounds overlap by a pre-determined amount.

5. The patient monitor of claim 3, wherein the acoustic analysis comprises a comparison of a volume of the ambient sounds to a volume of the default alarm signal, and the processor is configured to generate the new alarm signal having a volume greater than the volume of the ambient sounds if the volume of the ambient sounds is sufficient to mask the default alarm signal.

6. The patient monitor of claim 3, wherein the processor generates the new alarm signal from the default alarm signal on the fly in response to the analysis by adjusting one or more frequencies of the default alarm signal.

7. The patient monitor of claim 1, wherein the monitor is a pulse oximetry monitor.

8. The patient monitor of claim 1, wherein the processor is configured to add an overtone to the default alarm signal in generating the new alarm signal.

9. A patient monitoring system, comprising:
a patient monitor having:
a processor configured to generate a default alarm signal in response to patient physiological data indicative of an alarm condition, and configured to modify the default alarm signal to generate a new alarm signal in response to an ambient sounds input and patient physiological data indicative of the alarm condition, wherein the new alarm signal comprises a different frequency such that the new alarm signal has a different tone and/or pitch compared to the default alarm signal; and a user interface coupled to the processor and being operable to receive the new alarm signal generated by the processor and to provide a user-audible indication of the alarm condition, the user-audible indication being masked less by ambient sounds in an environment in which the patient monitor is located compared to the default alarm signal; and a sensor capable of being coupled to the patient monitor and being operable to collect the patient physiological data directly from a patient tissue.

10. The patient monitoring system of claim 9, wherein the sensor comprises a transducer separate from the sensing elements, the transducer being operable to capture the ambient sounds and provide the ambient sounds input to the processor, and wherein the processor is configured to perform an acoustic analysis of the ambient sounds and generate the new alarm signal in response to the analysis.

11. The patient monitoring system of claim 10, wherein the acoustic analysis comprises a comparison of frequencies of the ambient sounds to frequencies of the default alarm signal, and the processor is configured to generate the new alarm signal having different frequencies than the frequencies of the ambient sounds by generating a tone using one or more new frequencies.

12. The patient monitoring system of claim 10, wherein the acoustic analysis comprises a comparison of a volume of the ambient sounds to a volume of the default alarm signal, and the processor is configured to generate the new alarm signal having a volume greater than the volume of the ambient sounds if the volume of the ambient sounds is sufficient to mask the default alarm signal.

13. The patient monitoring system of claim 10, wherein the sensor comprises memory circuitry that is configured to provide information about the sensor to the patient monitor, wherein the information stored on the sensor places the monitor into a detection mode where the monitor periodically or substantially continuously performs the acoustic analysis of ambient sounds captured by the transducer.

14. A method of patient monitoring comprising:
monitoring a patient physiological parameter using a pulse oximetry monitoring system, wherein the pulse oximetry monitoring system comprises a pulse oximetry sensor configured to be disposed on a patient's tissue:
determining, with a processor of the pulse oximetry monitoring system, if an alarm condition exists based on measurements of the patient physiological parameter, wherein the alarm condition is associated with a default alarm signal;
capturing ambient sounds using the pulse oximetry monitoring system;
analyzing, with the processor, the captured ambient sounds to determine whether the ambient sounds will mask the default alarm signal of the alarm condition;
modifying, with the processor, the default alarm signal to generate a modified alarm signal as a new alarm signal having a different tone and/or pitch when the analysis determines that the ambient sounds will mask the default alarm signal; and
sounding the new alarm signal if the alarm condition exists, wherein the new alarm signal is selected to have a different frequency such that the new alarm signal has the different tone and/or pitch compared to the default alarm signal, wherein the pulse oximetry monitoring system is configured to sound the new alarm based on the analysis.

15. The method of claim 14, wherein analyzing the captured ambient sounds comprises:
generating a frequency spectrum of the captured ambient sounds;
comparing the frequency spectrum of the captured ambient sounds with a frequency spectrum of the default alarm signal;
identifying whether the frequencies of the captured ambient sounds overlap with frequencies of the default alarm signal; and
generating the new alarm signal having less than a predetermined amount of frequency overlap with the captured ambient sounds.

16. The method of claim 14, comprising generating the new alarm signal by selecting an alarm signal stored in a table.

17. The method of claim 16, wherein selecting an alarm signal stored in a table comprises:
comparing the frequency spectrum of the captured ambient sounds with frequency spectra of alarm signals stored in the table;
selecting an alarm signal having the least overlapping frequencies with the captured ambient sounds; and
adjusting a volume of the selected alarm signal if a volume of the captured ambient sounds is above a predetermined volume threshold.

18. The method of claim 16, wherein generating the new alarm signal comprises:
analyzing the frequency spectrum of the captured ambient sounds to identify available frequencies, the available frequencies comprising frequencies not emitted by the ambient sounds at a volume sufficient to mask the new alarm signal;
selecting a frequency from the available frequencies; and
synthesizing a tone based on the selected frequency.

* * * * *